US012805731B2

(12) United States Patent
Seomoon et al.

(10) Patent No.: US 12,805,731 B2
(45) Date of Patent: Nov. 24, 2026

(54) DISPLAY DEVICE

(71) Applicant: Samsung Display Co., Ltd., Yongin-si (KR)

(72) Inventors: Hee Seomoon, Yongin-si (KR); Chul Kim, Yongin-si (KR); Jin Oh Kwag, Yongin-si (KR); Tae Hee Lee, Yongin-si (KR); Hyeon Jun Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 708 days.

(21) Appl. No.: 17/348,216

(22) Filed: Jun. 15, 2021

(65) Prior Publication Data

US 2022/0047170 A1 Feb. 17, 2022

(30) Foreign Application Priority Data

Aug. 12, 2020 (KR) ........................ 10-2020-0101425

(51) Int. Cl.

| | |
|---|---|
| ***A61B 5/021*** | (2006.01) |
| ***A61B 5/00*** | (2006.01) |
| ***A61B 5/024*** | (2006.01) |

(52) U.S. Cl.

CPC .......... *A61B 5/021* (2013.01); *A61B 5/02433* (2013.01); *A61B 5/742* (2013.01)

(58) Field of Classification Search

CPC . A61B 5/02; A61B 2562/0233; A61B 5/0059; A61B 5/6898; A61B 5/02416; A61B 5/02433; A61B 5/742; A61B 5/14552; A61B 2562/0261; A61B 5/02108; A61B 5/02141; A61B 2562/046; A61B 2562/066; A61B 5/681; A61B 5/7445; A61B 2562/0247; A61B 5/021; G06F 3/14; G06F 3/147

USPC .......................................................... 600/485

See application file for complete search history.

(56) References Cited

U.S. PATENT DOCUMENTS

| | | | | |
|---|---|---|---|---|
| 8,711,069 | B2 * | 4/2014 | Park | H05K 1/0271 345/86 |
| 9,049,998 | B2 | 6/2015 | Brumback et al. | |
| 9,214,499 | B2 | 12/2015 | Jeung et al. | |
| 9,974,482 | B2 | 5/2018 | Shim et al. | |
| 10,398,324 | B2 | 9/2019 | Mukkamala et al. | |
| 10,635,212 | B2 | 4/2020 | Hong et al. | |
| 10,813,561 | B2 | 10/2020 | Kwon et al. | |
| 11,337,609 | B2 | 5/2022 | Choi et al. | |

(Continued)

FOREIGN PATENT DOCUMENTS

| | | |
|---|---|---|
| CN | 108236460 A | 7/2018 |
| CN | 110381817 A | 10/2019 |

(Continued)

*Primary Examiner* — Jacqueline Cheng
*Assistant Examiner* — Jonathan E. Cooper
(74) *Attorney, Agent, or Firm* — Womble Bond Dickinson (US) LLP

(57) ABSTRACT

A display device includes: a display panel having a plurality of light emitting elements to display an image, the display panel including a first area; a blood pressure sensor disposed adjacent to the display panel to sense pressure applied to at least a portion of the first area and to sense light incident thereon; and a pressure transmission member overlapping the first area of the display panel and the blood pressure sensor.

29 Claims, 29 Drawing Sheets

(56) References Cited

U.S. PATENT DOCUMENTS

| | | | | |
|---|---|---|---|---|
| 2011/0214501 | A1* | 9/2011 | Ross | A61B 5/6807 73/172 |
| 2013/0296714 | A1* | 11/2013 | Kassim | G01N 21/3151 600/479 |
| 2014/0313463 | A1* | 10/2014 | Jang | G02F 1/136209 349/106 |
| 2014/0346478 | A1* | 11/2014 | Cho | H01L 27/1248 257/40 |
| 2017/0027521 | A1 | 2/2017 | Geva et al. | |
| 2017/0119307 | A1 | 5/2017 | Shim et al. | |
| 2017/0319079 | A1* | 11/2017 | Mezenok | A61B 5/6898 |
| 2017/0325698 | A1* | 11/2017 | Allec | A61B 5/721 |
| 2018/0184920 | A1* | 7/2018 | Rabinovich | A61B 5/02438 |
| 2019/0008399 | A1* | 1/2019 | Mukkamala | A61B 5/0261 |
| 2019/0012029 | A1* | 1/2019 | Hong | G06F 3/0412 |
| 2019/0095674 | A1* | 3/2019 | Ko | H10K 59/40 |
| 2019/0104997 | A1* | 4/2019 | Kang | A61B 5/6826 |
| 2020/0272276 | A1* | 8/2020 | Goeltner | A61B 5/6898 |
| 2021/0059537 | A1* | 3/2021 | Nakagawa | A61B 5/022 |

FOREIGN PATENT DOCUMENTS

| | | | | |
|---|---|---|---|---|
| JP | 2007209374 | A | * | 8/2007 |
| KR | 10-2010-0093165 | A | | 8/2010 |
| KR | 10-2014-0101605 | | | 8/2014 |
| KR | 10-2017-0049280 | | | 5/2017 |
| KR | 10-2018-0063053 | | | 6/2018 |
| KR | 10-2019-0006123 | A | | 1/2019 |
| KR | 10-2022394 | | | 9/2019 |
| KR | 10-2020-0092665 | A | | 8/2020 |

* cited by examiner

BUMP: P_BUMP

DISPLAY DEVICE

CROSS REFERENCE TO RELATED APPLICATION

This application claims priority from and the benefit of Korean Patent Application No. 10-2020-0101425, filed on Aug. 12, 2020, which is hereby incorporated by reference for all purposes as if fully set forth herein.

BACKGROUND

Field

Implementations of the invention relate generally to a display device and, more specifically, to a display device including a sensor, such as a blood pressure sensor.

Discussion of the Background

Recently, as interest in health management has increased, there is an increasing interest and demand for a healthcare device for checking and managing user's health anytime and anywhere. A technology for monitoring health status in users by providing various sensors in a display device such as a smart watch is being developed.

A photoplethysmographic sensor, may measure an amount of blood flowing through a blood vessel based on light reflected from the blood vessel by irradiating light into the blood vessel, and measure heart rate based on the change in blood volume according to a change in volume of the blood vessel that occur when the heart relaxes and contracts.

The above information disclosed in this Background section is only for understanding of the background of the inventive concepts, and, therefore, it may contain information that does not constitute prior art.

SUMMARY

Applicant realized that in order to measure an absolute value associated with blood flow, that is, blood pressure, with relatively high reliability, preliminary work and/or preprocesses such as calibration for a blood volume measured from a photo-electromyography is required, or an additional device such as a cuff is required.

Display devices constructed according to the principles and illustrative implementations of the invention are capable of more efficiently measuring blood pressure. For example, the display device may accurately measure the blood pressure without performing preliminary work and/or preprocesses such as calibration or without using an additional device such as a cuff. For example, the display device may include a blood pressure sensor and a pressure transmission member overlapping the blood pressure sensor to help the blood pressure sensor and its driver to measure the blood pressure with relatively high reliability. More specifically, the blood pressure sensor may include a pressure sensor to sense pressure of touch of user's body and a photo sensor to sense light reflected by the body. The display device may determine blood volume from the sensed light and may generate a signal of the blood pressure based on a change in the blood volume according to the pressure. A pressure transmission member overlapping the blood pressure sensor may improve sensitivity of the pressure sensor. In addition, a display panel of the display device may include a hole (or an opening) overlapping the photo sensor to improve sensitivity of the photo sensor. Accordingly, the display device may measure the blood pressure accurately, with relatively high reliability and without additional components typically required in the related art.

Additional features of the inventive concepts will be set forth in the description which follows, and in part will be apparent from the description, or may be learned by practice of the inventive concepts.

According to one aspect of the invention, a display device includes: a display panel having a plurality of light emitting elements to display an image, the display panel including a first area; a blood pressure sensor disposed adjacent to the display panel to sense pressure applied to at least a portion of the first area and to sense light incident thereon; and a pressure transmission member overlapping the first area of the display panel and the blood pressure sensor.

The pressure transmission member may include a metallic material.

The pressure transmission member may be disposed between the display panel and the blood pressure sensor.

The pressure transmission member may include a bump having a planar size smaller than or equal to that of the blood pressure sensor.

The blood pressure sensor may be disposed under the display panel and may include: a first sensor disposed under the pressure transmission member to sense pressure; and a second sensor disposed under the first sensor to sense light transmitted through the display panel.

The second sensor may include a photo sensor including a light source to emit infrared light or green light.

The second sensor may include a photo sensor to sense light emitted from the display panel and then reflected from a target object.

The display device may further include a driver to calculate blood pressure based on a pressure sensing signal provided from the first sensor and a light sensing signal provided from the second sensor.

The first sensor may include a pressure sensor including first electrodes extending in a first direction and second electrodes extending in a second direction intersecting the first direction and partially overlapping the first electrodes. The pressure transmission member may include patterns that are spaced apart from each other in a plan view, and the patterns may be respectively disposed in second areas in which the first and second electrodes overlap each other in a plan view.

Each of the patterns may include a bump pattern having a planar size smaller than or equal to that of each of the second areas.

The display panel may include a first hole disposed in the first area of the display panel.

The pressure transmission member may include a second hole overlapping the first hole.

The pressure transmission member may include patterns that are spaced apart from each other in a plan view, and the patterns may be arranged along an edge of the second hole.

The first sensor may include a pressure sensor including first electrodes extending in a first direction in a plan view and second electrodes extending in a second direction intersecting the first direction and partially overlapping the first electrodes, and the patterns may be respectively disposed in second areas in which the first and second electrodes overlap in a plan view.

The patterns may include third holes.

The pressure transmission member may include patterns that are spaced apart from each other in a plan view, and the patterns may be disposed over the first area excluding the second hole.

The display panel may include openings disposed in the first area of the display panel without overlapping the light emitting elements and conductive patterns connected to the light emitting elements.

The display panel may include a light-transmissive material inside each of the openings, and the light-transmissive material may include at least one of germanium, silicon, zinc selenide (ZnSe), silicon dioxide (SiO2), polyethylene, and polystyrene.

The pressure transmission member may include patterns that are spaced apart from each other in a plan view, and each of the patterns may be disposed between adjacent ones of the openings in a plan view.

The pressure transmission member may include patterns that are spaced apart from each other in a plan view, and each of the patterns may be disposed to overlap some of the openings in a plan view.

The patterns may include third hole overlapping the some of the openings.

The display device may further include: a bracket disposed under the blood pressure sensor, the pressure transmission member may be disposed between the blood pressure sensor and the bracket.

The blood pressure sensor may include: a first sensor disposed under the pressure transmission member to sense the pressure; and a second sensor disposed under the first sensor to sense the light. The pressure transmission member may be disposed between the first sensor and the second sensor.

The display device may further include: a window disposed on the display panel. The pressure transmission member may be disposed between the display panel and the window.

The display panel may include: a first substrate; a light emitting element layer disposed on the first substrate and including the light emitting elements; a first passivation layer disposed on the light emitting element layer; and a second passivation layer disposed under the first substrate. The pressure transmission member may be disposed between the substrate and the second passivation layer.

According to another aspect of the invention, a display device includes: a display panel having a plurality of light emitting elements to display an image, the display panel including a first area; a pressure sensor disposed on the display panel to sense a pressure applied to at least a portion of the first area; a photo sensor disposed under the display panel to sense light incident thereon; a pressure transmission member disposed on the display panel and overlapping the pressure sensor; and a driver to generate a blood pressure signal based on a pressure sensing signal provided from the pressure sensor and a light sensing signal provided from the photo sensor.

The display device may further include: a window disposed on the pressure sensor, and the pressure transmission member may be disposed between the window and the pressure sensor.

The pressure transmission member may be disposed between the pressure sensor and the display panel.

The display panel may include a first hole disposed in the first area of the display panel.

The pressure transmission member may include a second hole overlapping the first hole.

The pressure transmission member may include patterns that are spaced apart from each other in a plan view, and the patterns may be arranged along an edge of the second hole.

The pressure sensor may include first electrodes extending in a first direction in a plan view and second electrodes extending in a second direction intersecting the first direction and partially overlapping the first electrodes, and the patterns may be respectively disposed in second areas in which the first and second electrodes overlap each other in a plan view.

The patterns may include third holes.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
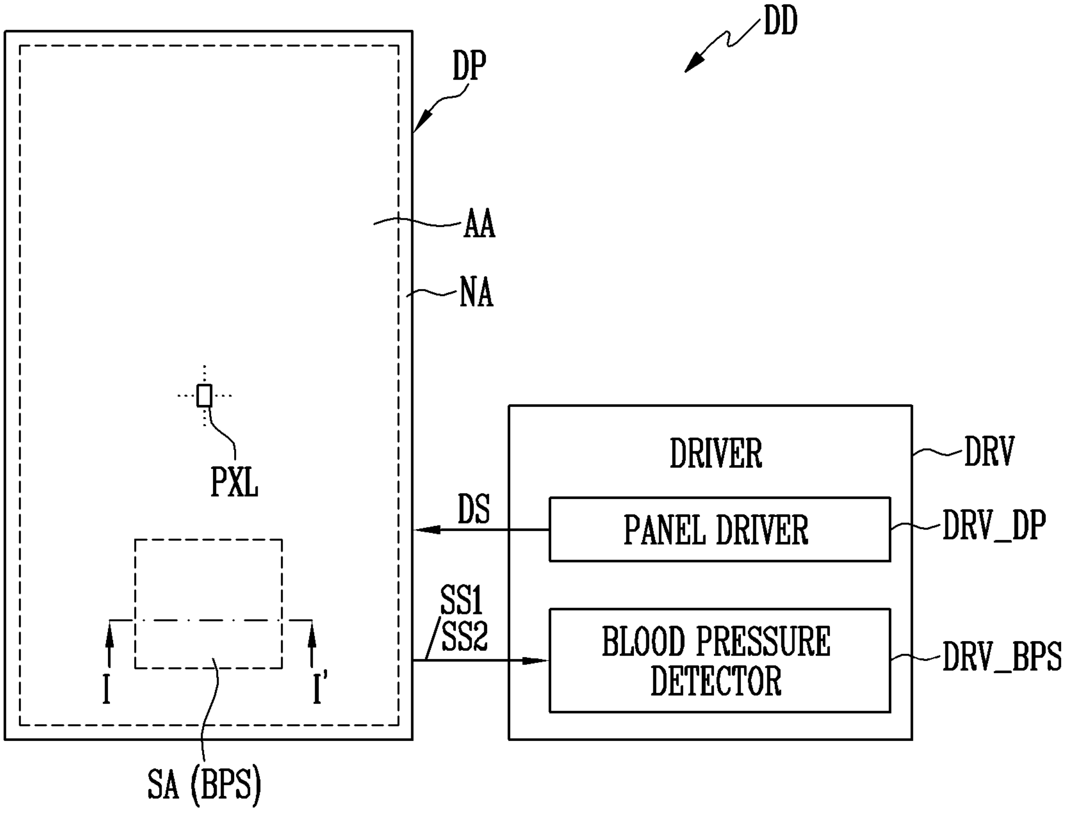
FIG. 1 is a block diagram of an embodiment of a display device constructed according to the principles of the invention.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 2:
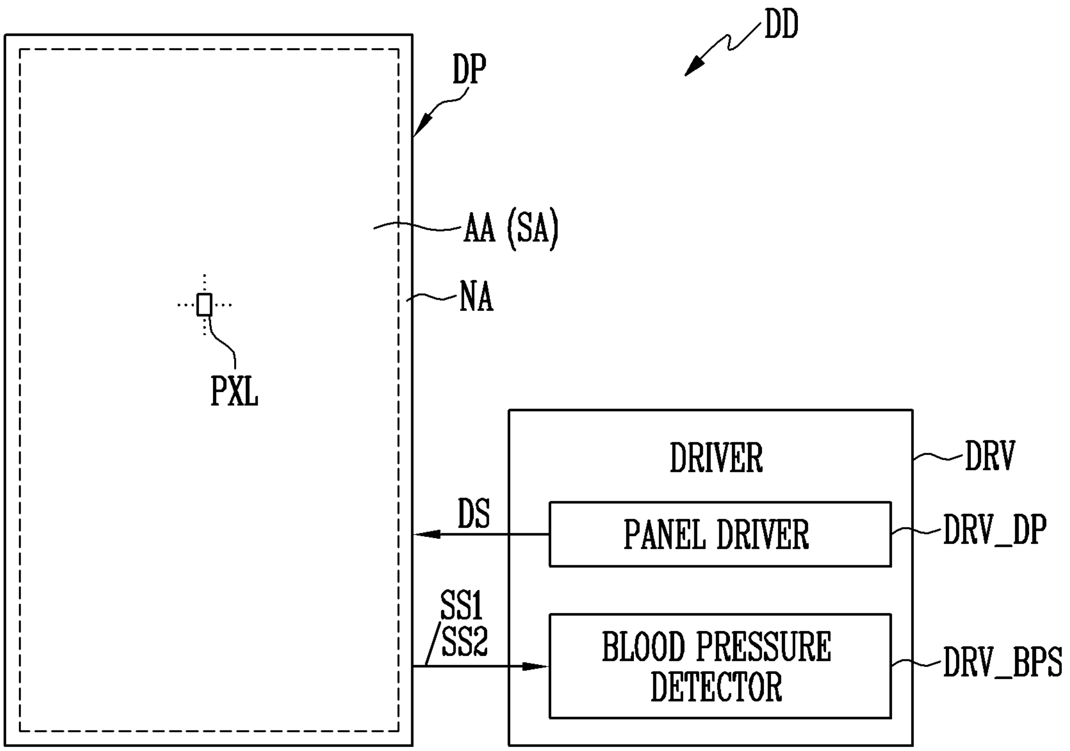
FIG. 2 is a block diagram of another embodiment of the display device of FIG. 1.

FIG. 1 is a block diagram of an embodiment of a display device constructed according to the principles of the invention. FIG. 2 is a block diagram of another embodiment of the display device of FIG. 1. For convenience, in FIG. 1 and FIG. 2, a display panel DP and a driver DRV are illustrated as separate components, but embodiments are not limited thereto. For example, all or a portion of the driver DRV may be integrally implemented on the display panel DP.

Referring to FIG. 1 and FIG. 2, a display device DD may include the display panel DP and the driver DRV. The driver DRV may include a panel driver DRV_DP and a blood pressure detector DRV_BPS, which is a driver for a blood pressure sensor.

All or at least a portion of the display device DD may be flexible.

The display panel DP includes a display area AA and a non-display area NA. The display area AA is an area in which a plurality of pixels PXL (or subpixels) are provided, and may be referred to as an active area. In various embodiments, each of the pixels PXL may include at least one light emitting element. The display device DD displays an image in the display area AA by driving the pixels PXL in response to image data inputted from the outside.

In an embodiment, the display area AA may include a sensing area SA (or a first area). The sensing area SA may include at least some of the pixels PXL provided in the display area AA.

In an embodiment, as shown in FIG. 1, at least a portion of the display area AA may be set as the sensing area SA. In another embodiment, as shown in FIG. 2, all of the display area AA may be set as the sensing area SA. In this case, a blood pressure measurement operation may be performed only in a portion that is substantially touched by a user.

FIG. 1 illustrates an example in which only one sensing area SA is formed in the display area AA, but embodiments are not limited thereto. For example, a plurality of sensing areas SA may be regularly or randomly arranged in the display area AA.

In addition, FIG. 1 illustrates an example in which the sensing area SA is formed in at least some of the display area AA, but embodiments are not limited thereto. That is, in various embodiments, the display area AA and the sensing area SA may partially overlap each other.

The non-display area NA is an area disposed at least partially around the display area AA, and may be referred to as a non-active area. For example, the non-display area NA may include a wire area, a pad area, and various dummy areas.

The display device DD may further include a blood pressure sensor BPS provided in the sensing area SA.

The blood pressure sensor BPS may sense a pressure applied to at least a portion of the sensing area SA by part of a user's body, and sense reflected light incident through the display panel DP from the body part. The blood pressure sensor BPS may include a pressure sensor that senses pressure and a photo sensor that senses reflected light.

When a pressure is applied to the sensing area SA by a user's body part (for example, finger), the pressure sensor may sense an area to which the pressure is applied and a magnitude of the pressure (that is. a pressure value, force), and output a first sensing signal SS1, which is an electrical signal (for example, a voltage signal). The first sensing signal SS1 having different electrical characteristics according to the pressure may be outputted. The pressure sensor may be implemented as a general strain gauge type of pressure sensor or a capacitive type of pressure sensor.

The display device DD may further include a pressure transmission member, which may be in the form of a bump, provided in the sensing area SA. The bump may allow the pressure to be concentrated on and/or transmitted effectively and efficiently to the pressure sensor in the sensing area SA without dispersing the pressure over a larger area. Therefore, sensitivity of the pressure sensor may be improved. The bump will be described later with reference to FIG. 3A.

When light emitted from a light source provided in the photo sensor or a light source (for example, the pixel PXL) provided in the display device DD is reflected by the part of the user's body, the photo sensor may sense the reflected light to output a second sensing signal SS2, which is an electrical signal (for example, a voltage signal). The second sensing signal SS2 having different electrical characteristics may be outputted according to the blood volume flowing through a blood vessel in a part of the user's body touching the display device DD. The photo sensor may be implemented as a general photoplethysmographic sensor (for example, PPG sensor).

In some embodiments, the display panel DP may include a hole formed in the sensing area SA. Here, the hole may include a physical hole physically penetrating the display panel DP or an optical hole (for example, microscopic hole having a diameter of tens to hundreds of μm) which do not overlap the light emitting elements and conductive patterns (for example, wires) connected to the light emitting elements.

The hole may form an optical system that provides a light path by condensing light directed to the blood pressure sensor BPS. A condensing rate of light incident on the blood pressure sensor BPS may be improved by the optical system. In some embodiments, the optical system may be formed of an optical fiber, silicon, and the like. The amount of reflected light passing through the display panel DP via the hole increases, and the sensitivity of the photo sensor may be improved by the optical system. The hole formed in the display panel DP will be described later with reference to FIG. 12A.

In some embodiments, the photo sensor may use the light emitting element provided in the pixel PXL as a light source. In these embodiments, the photo sensor may form a photoplethysmographic sensor with the light emitting elements provided in pixels PXL. As such, when the pixels PXL are used as light sources without separate external light sources, volumes of the photo sensor and the blood pressure sensor BPS including the photo sensor may be reduced, and thus manufacturing costs may be reduced.

In various embodiments, the blood pressure sensor BPS may be disposed on a surface (for example, a rear surface) opposite to another surface (for example, a front surface) on which an image is displayed among respective surfaces of the display panel DP. However, embodiments are not limited thereto. For example, at least some (for example, the pressure sensor) of the blood pressure sensor BPS may be disposed adjacent to the front surface of the display panel DP compared to the pixels PXL.

The driver DRV may drive the display panel DP. For example, the driver DRV may output a data signal DS corresponding to image data to the display panel DP. In addition, the driver DRV may output a driving signal for driving the blood pressure sensor BPS, and may receive electrical signals (for example, the first sensing signal SS1 provided from the pressure sensor and the second sensing signal SS2 provided from the photo sensor) from the blood pressure sensor BPS. The driver DRV may measure a user's blood pressure by using the electrical signals.

In some embodiments, the driver DRV may include the panel driver DRV_DP and the blood pressure detector DRV_BPS. Each of the panel driver DRV_DP and the blood pressure detector DRV_BPS may be implemented as an integrated circuit, and may be mounted on a flexible circuit board. The panel driver DRV_DP may be connected to the display panel DP through the flexible circuit board, and the blood pressure detector DRV_BPS may be connected to the blood pressure sensor BPS through the flexible circuit board. In FIG. 1 and FIG. 2, the panel driver DRV_DP and the blood pressure detector DRV_BPS are separately shown, but embodiments are not limited thereto. For example, at least a portion of the blood pressure detector DRV_BPS may be integrated with the panel driver DRV_DP, or may operate in conjunction with the panel driver DRV_DP.

The panel driver DRV_DP may supply the data signal DS corresponding to image data to the pixels PXL while sequentially scanning the pixels PXL of the display area AA. Thus, the display panel DP may display an image corresponding to the image data.

In an embodiment, the panel driver DRV_DP may supply a driving signal for blood pressure measurement to the pixels PXL. The driving signal may be provided so that the pixels PXL emit light to operate as the light source for measuring blood pressure. In this case, the driving signal for measuring blood pressure may be provided to the pixels PXL provided in a specific area within the display panel DP (for example, the pixels (PXL) provided in the sensing area SA).

The blood pressure detector DRV_BPS may measure blood pressure based on electrical signals (for example, the first sensing signal SS1 provided from the pressure sensor and the second sensing signal SS2 provided from the photo sensor) from the blood pressure sensor BPS. For example, the blood pressure detector DRV_BPS may calculate a pressure value (that is, force) and an area to which pressure is applied based on the first sensing signal SS1; calculate a pressure (for example, pressure=force/area) based on the pressure value and the area; calculate a blood volume based on the second sensing signal SS2; and calculate a blood pressure based on the change in the blood volume according to the pressure.

As described above with reference to FIG. 1 and FIG. 2, the display device DD includes the blood pressure sensor BPS including the pressure sensor that senses pressure and the photo sensor that senses light, and the blood pressure detector DRV_BPS may calculate the blood pressure based on a change in blood volume according to the pressure.

In addition, in the display device DD, the sensitivity of the pressure sensor may be improved by using the bump, and the sensitivity of the photo sensor may be improved by using the hole formed in the display panel DP. Therefore, the blood pressure may be measured more accurately.

Figure 3A:
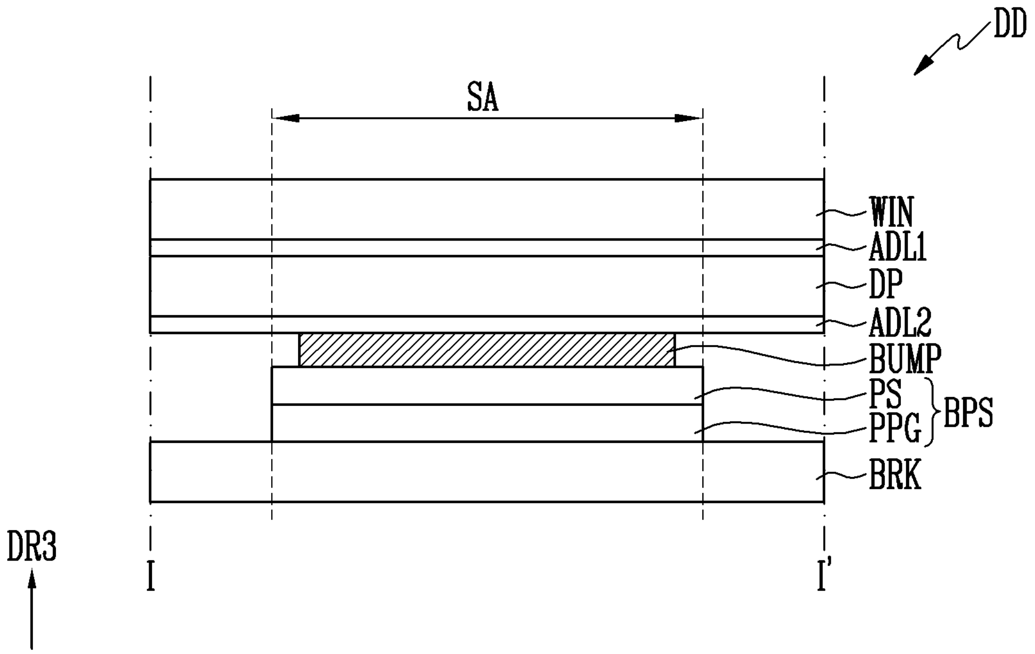
FIG. 3A and FIG. 3B are cross-sectional views of embodiments of the display device taken along line I-I' of FIG. 1.
Figure 3B:
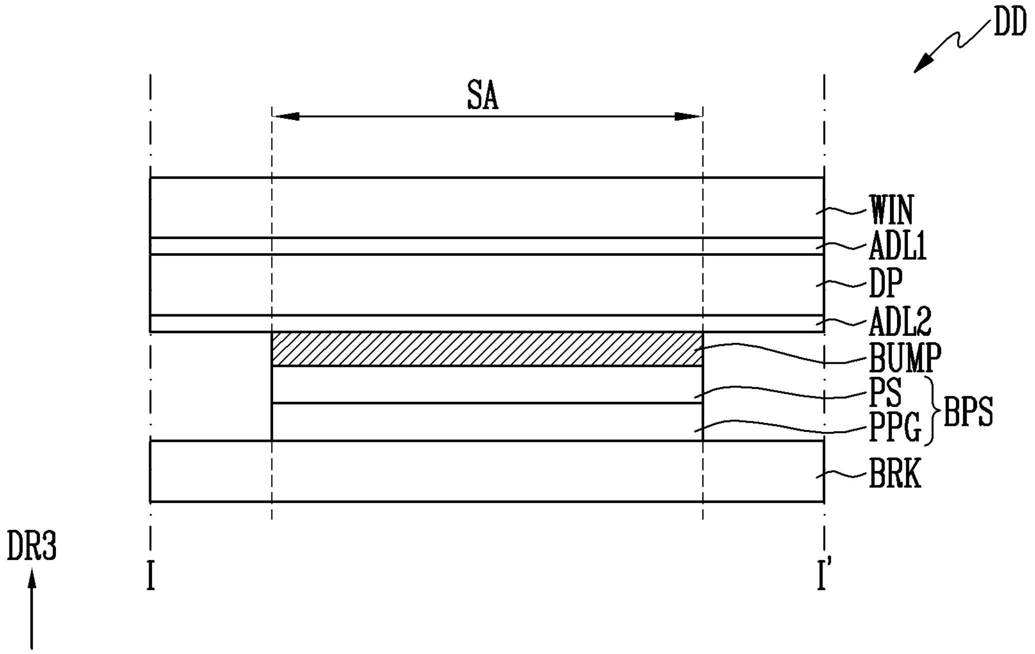

FIG. 3A and FIG. 3B are cross-sectional views of embodiments of the display device taken along line I-I' of FIG. 1.

Referring to FIG. 1, FIG. 3A, and FIG. 3B, a display device DD may include the display panel DP, a window WIN, the blood pressure sensor BPS, and a pressure transmission member which may be in the form of a bump BUMP. In addition, the display device DD may further include a bracket BRK.

As used herein, "an upper portion" and "an upper surface" in a thickness direction mean a display surface side or a third direction DR3 side with respect to the display panel DP, and "a lower portion" and "a lower surface" mean a side opposite to the display surface or a direction opposite to the third direction DR3 with respect to the display panel DP. In addition, "upper (top)", "lower (bottom)", "left", and "right" in a planar direction mean directions when viewed from a top side with the display surface in a normal position.

The display panel DP is a panel that displays an image, and for example, an organic light emitting display panel may be applied. Hereinafter, a case in which an organic light emitting display panel is applied as the display panel DP is exemplified, but embodiments are not limited thereto, and other types of display panels such as a liquid crystal display (LCD) and an inorganic light emitting display device may be applied.

Figure 4:
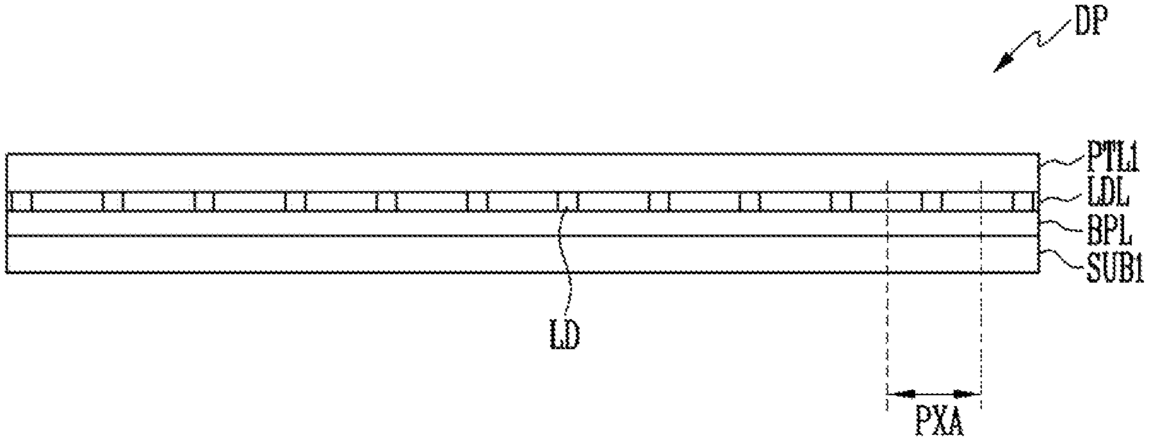
FIG. 4 is a cross-sectional view of an embodiment of the display panel of FIG. 3A.

FIG. 4 may be referred to explain a more specific configuration of the display panel DP.

FIG. 4 is a cross-sectional view of an embodiment of the display panel of FIG. 3A.

Referring to FIG. 1, FIG. 3A, and FIG. 4, a display panel DP may include a first substrate SUB1, a circuit element layer BPL, a light emitting element layer LDL, and a first passivation layer PTL1.

The first substrate SUB1 is a base substrate for the display panel DP, and may be a substantially transparent transmissive substrate. The first substrate SUB1 may be a rigid substrate including glass or tempered glass, or a flexible substrate made of plastic material. However, the material of the first substrate SUB1 is not limited thereto, and the first substrate SUB1 may be made of various materials.

The circuit element layer BPL may be disposed on an upper surface of the first substrate SUB1, and may include at least one conductive layer. For example, the circuit element layer BPL may include a plurality of circuit elements forming a pixel circuit of the pixels PXL, and wires for supplying various power sources and signals for driving the pixels PXL. In this case, the circuit element layer BPL may include various circuit elements such as at least one transistor and capacitor, and a plurality of conductive layers for forming wires connected to the various circuit elements. In addition, the circuit element layer BPL may include at least one insulation layer provided between the plurality of conductive layers.

The light emitting element layer LDL may be disposed on an upper surface of the circuit element layer BPL. The light emitting element layer LDL may include a plurality of light emitting elements LD connected to circuit elements and/or wires of the circuit element layer BPL through a contact hole or the like.

In an embodiment, at least one of the light emitting elements LD may be provided for each pixel PXL (or pixel area PXA). For example, the light emitting element LD may be configured of an organic light emitting diode or an inorganic light emitting diode such as a micro light emitting diode and a quantum dot light emitting diode. In addition, the light emitting element LD may be a light emitting element complexly made of organic and inorganic materials. Further, each pixel PXL may include a single light emitting element, or in another embodiment, each pixel PXL may include a plurality of light emitting elements, and the plurality of light emitting elements may be connected in series, parallel, or in series and parallel to each other.

The first passivation layer PTL1 may be disposed on the light emitting element layer LDL to cover the display area AA. The first passivation layer PTL1 may include a sealing member such as a thin film encapsulation (TFE) or encapsulation substrate, and may additionally include a protective film in addition to the sealing member.

Referring back to FIG. 3A and FIG. 3B, a first adhesive layer ADL1 may be disposed between the display panel DP (or the first passivation layer PTL1, see FIG. 4) and the window WIN to combine the display panel DP and the window WIN. The first adhesive layer ADL1 may include a transparent adhesive such as an optical clear adhesive (OCA), and may include various adhesive materials.

The window WIN may be a protective member disposed at an uppermost portion of the display device DD including the display panel DP, and may be a substantially transparent transmissive substrate. The window WIN may have a multi-layered structure selected from a glass substrate, a plastic film, and a plastic substrate. The window WIN may include a rigid or flexible substrate, and the material included in the window WIN is not particularly limited.

In various embodiments, the display device DD may further include a polarizing plate, an anti-reflection layer, and/or a touch sensor layer (touch electrode layer), which are not shown. For example, the display device DD may further include a polarizing plate and/or touch sensor layer disposed between the display panel DP and the window WIN.

In various embodiments, a selective light blocking film may be further provided under the display panel DP. The selective light blocking film may block a specific frequency band, for example, infrared rays in external light directed to the display device DD to prevent the corresponding light from being directed to the blood pressure sensor BPS.

The blood pressure sensor BPS may be disposed on a lower surface (e.g., rear surface) of the display panel DP to overlap at least a portion of the display panel DP. The blood pressure sensor BPS may overlap the display panel DP in the sensing area SA. The sensing area SA may be defined as an area in which the blood pressure sensor BPS and the display panel DP overlap.

In some embodiments, the blood pressure sensor BPS may include a pressure sensor PS and a photo sensor PPG (or photoplethysmographic sensor).

The pressure sensor PS may be disposed under the display panel DP to sense the pressure applied to the sensing area SA, and the photo sensor PPG may be disposed under the pressure sensor PS to sense reflected light incident through the sensing area SA. The photo sensor PPG may overlap at least a portion of the pressure sensor PS, and as shown in FIG. 3A, the photo sensor PPG may completely overlap the pressure sensor PS. However, embodiments are not limited thereto, and the photo sensor PPG may be larger or smaller than the pressure sensor PS.

Figure 5A:
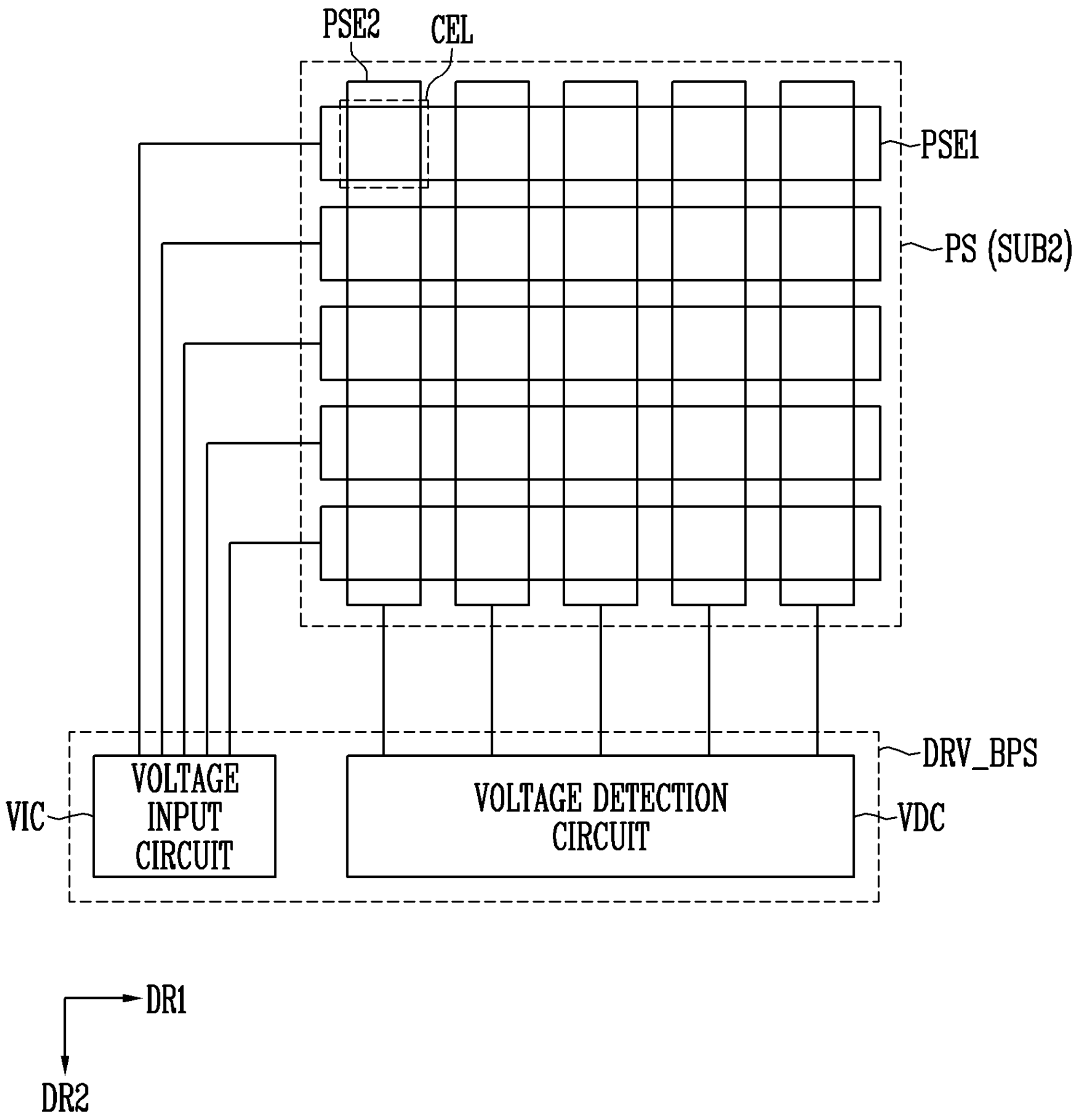
FIG. 5A is a plan view of an embodiment of the pressure sensor of FIG. 3A.
Figure 5B:
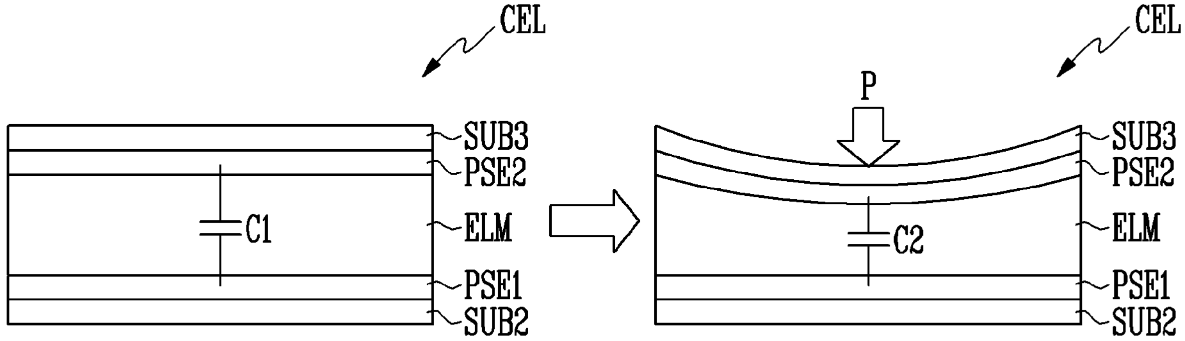
FIG. 5B schematically illustrates cross-sectional views of an embodiment of the pressure sensor of FIG. 5A, which is deformable depending on pressure.

FIG. 5A and FIG. 5B may be referred to explain a specific configuration of the pressure sensor PS.

FIG. 5A is a plan view of an embodiment of the pressure sensor of FIG. 3A. FIG. 5B schematically illustrates cross-sectional views of an embodiment of the pressure sensor of FIG. 5A, which is deformable depending on pressure.

Referring to FIG. 1, FIG. 3A, FIG. 5A, and FIG. 5B, a pressure sensor PS may include a second substrate SUB2, first electrodes PSE1, an elastic layer ELM, second electrodes PSE2, and a third substrate SUB3. The blood pressure detector DRV_BPS may include a voltage input circuit VIC and a voltage detection circuit VDC.

The second substrate SUB2 and the third substrate SUB3 are base substrates for the pressure sensor PS, and they may be transparent transmissive substrates. The second substrate SUB2 and the third substrate SUB3 may be flexible substrates made of a plastic material. However, the materials of the second substrate SUB2 and the third substrate SUB3 are not limited thereto, and the second substrate SUB2 and the third substrate SUB3 may be made of various materials.

The first electrodes PSE1 may be disposed on the second substrate SUB2, may extend in a first direction DR1, and may be spaced apart from each other along a second direction DR2. The second electrodes PSE2 may be disposed under the third substrate SUB3, may extend in the second direction DR2, and may be spaced apart from each other along the first direction DR1. The second electrodes PSE2 may partially overlap the first electrodes PSE1, and the first electrodes PSE1 and the second electrodes PSE2 may be spaced apart without directly contacting each other.

In some embodiments, the first electrodes PSE may be driving electrodes, and the second electrodes PSE2 may be sensing electrodes. The first electrodes PSE1 and the second electrodes PSE2 may include a conductive material such as silver (Ag), copper (Cu), aluminum (Al), and a conductivity polymer.

The elastic layer ELM may be disposed between the first electrodes PSE1 and the second electrode PSE2. The elastic layer ELM may include an elastic material having a relatively small modulus.

Sensing cells CEL (or nodes, pressure sensing nodes) may be formed in each of areas in which the first electrodes PSE1 and the second electrodes PSE2 overlap. The sensing cells CEL may independently sense a pressure of a corresponding position.

The first electrodes PSE1 may be electrically connected to the voltage input circuit VIC, and a specific voltage may be applied to the first electrodes PSE1 from the voltage input circuit VIC. The second electrodes PSE2 may be electrically connected to the voltage detection circuit VDC, and an electrical signal corresponding to the specific voltage may be outputted to the voltage detection circuit VDC from the second electrode PSE2.

As shown in FIG. 5B, when a touch input is generated on the sensing cell CEL, the gap between the first electrode PSE1 and the second electrode PSE2 is changed by the pressure of the touch input, and accordingly, capacitance of the sensing cell CEL may be changed from a first capacitance C1 to a second capacitance C2. The voltage detection circuit VDC may sense pressure based on a change in capacitance.

In another embodiment, the elastic layer ELM may include a pressure sensitive material. The pressure sensitive material may contain metal nanoparticles such as nickel, aluminum, tin, and copper, or carbon. The pressure-sensitive material may be disposed in a polymer resin in the form of particles, but is not limited thereto.

When the elastic layer ELM includes a pressure sensitive material, electrical resistance of the elastic layer ELM decreases as the pressure increases, and thus the magnitude of the pressure may be sensed. For example, when pressure is applied to the sensing cell CEL, the gap between the first electrode PSE1 and the second electrode PSE2 decreases, and the first electrode PSE1 and the second electrode PSE2 may be electrically connected through the pressure sensitive material in the elastic layer ELM or the electrical conductivity between the first electrode PSE1 and the second electrode PSE2 may increase. That is, the elastic layer ELM between the first electrode PSE1 and the second electrode PSE2 may act as a variable resistor according to pressure. Therefore, the voltage detection circuit VDC may sense the amount of current flowing through the first electrode PSE1, the elastic layer ELM, and the second electrode PSE2 from the voltage input circuit VIC, or may convert the amount of current into a voltage to sense pressure.

Figure 6A:
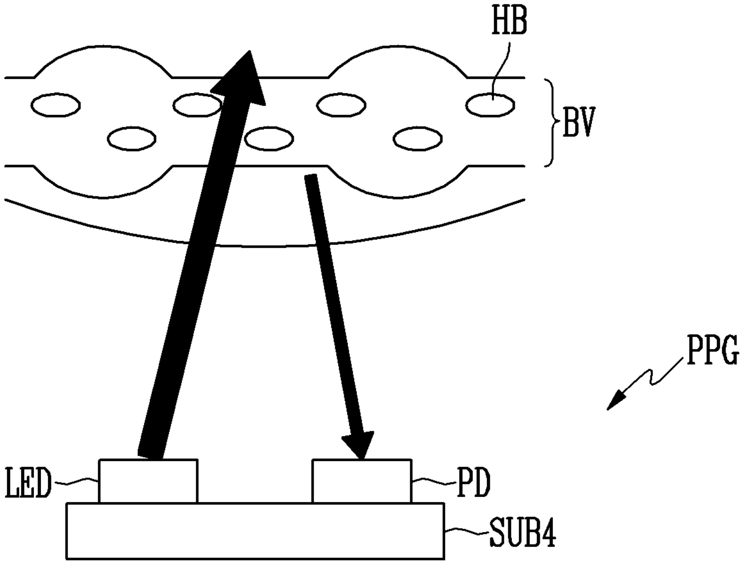
FIG. 6A and FIG. 6B are cross-sectional views of an embodiment the photo sensor of FIG. 3A and a blood vessel adjacent to the photo sensor.
Figure 6B:
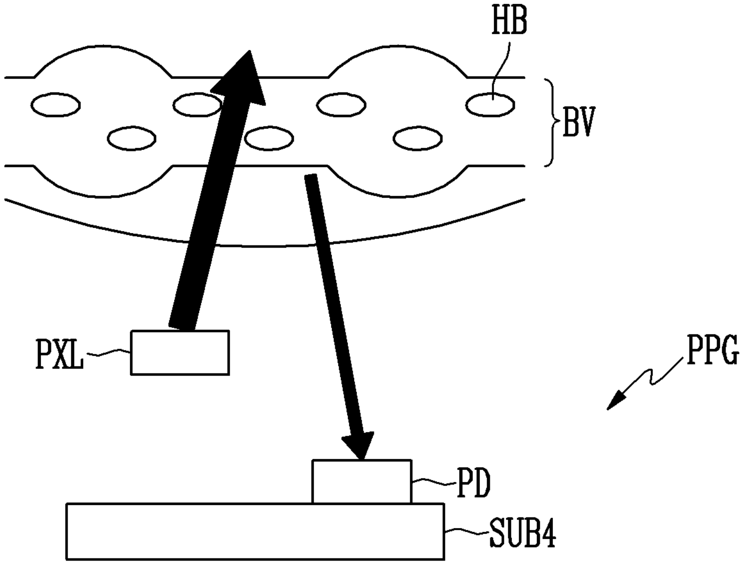

In order to explain a specific configuration and operation of the photo sensor PPG (or photoplethysmographic sensor), reference is made to FIG. 6A and FIG. 6B.

FIG. 6A and FIG. 6B are cross-sectional views of an embodiment the photo sensor of FIG. 3A and a blood vessel adjacent to the photo sensor.

Referring to FIG. 6A, a photo sensor PPG may include a fourth substrate SUB4, and a light emitting portion LED and a light receiving portion PD that are spaced apart from each other on the fourth substrate SUB4.

The light emitting portion LED may emit light to irradiate the light upon a part of the user's body (for example, a finger). For example, the light emitting portion LED may include at least one of a light emitting diode, an organic light emitting diode (OLED), an infrared emitting diode, and a laser diode.

The light receiving portion PD may sense light reflected by a part of the user's body by being irradiated from the light emitting portion LED, and may output an electrical signal corresponding to the reflected light. For example, the light receiving portion PD may be implemented as an organic photodiode.

In some embodiments, the light emitting portion LED may emit infrared rays or green light. In an embodiment, the light emitting portion LED may emit infrared rays. In this case, since red blood cells (or hemoglobin HB) in a blood vessel BV absorb infrared rays, the amount of absorption of the infrared rays may be measured through the light receiving portion PD. In another embodiment, the light emitting portion LED may emit green light. In this case, since the red blood cells (or hemoglobin HB) absorb green light, the amount of absorption of the green light may be measured through the light receiving portion PD.

FIG. 6A illustrates the case in which the photo sensor PPG includes the light emitting portion LED, but the photo sensor PPG is not limited thereto. As shown in FIG. 6B, the photo sensor PPG may not include the light emitting portion LED. In this case, light (for example, green light) may be emitted from the pixel PXL in the sensing area SA (see FIG. 1) of the display panel DP, and the light receiving portion PD may sense light emitted by the pixel PXL and reflected by a part of the user's body (or a target object).

Referring back to FIG. 3A, the bump BUMP may overlap the blood pressure sensor BPS and/or the pressure sensor PS.

In some embodiments, as shown in FIG. 3A, the bump BUMP may be disposed between the display panel DP and the blood pressure sensor BPS. The bump BUMP may concentrate pressure applied to the sensing area SA on the pressure sensor PS within the sensing area SA without distributing the pressure applied to the sensing area SA.

The bump BUMP may be attached to a lower surface of the display panel DP through a second adhesive layer ADL2. The second adhesive layer ADL2 may include a transparent adhesive such as OCA, and may include various adhesive materials. In another embodiment, the bump BUMP may be formed through coating or printing on the lower surface of the display panel DP.

In some embodiments, the bump BUMP may include a material having a relatively large modulus. For example, the bump BUMP may have a modulus greater than that of the elastic layer ELM of the pressure sensor PS shown in FIG. 5B. That is, the bump BUMP may include a material that does not deform by repeated pressing. In an embodiment, the bump BUMP may be made of a metallic material such as copper or aluminum, or a conductive material. In another embodiment, the bump BUMP may be made of a polymer resin such as an acryl resin or an epoxy resin.

In some embodiments, the planar size of the bump BUMP may be smaller than or substantially equal to that of the blood pressure sensor BPS (or that of the sensing area SA corresponding thereto). In an embodiment, as shown in FIG. 3A, the width (or a planar size corresponding thereto) of the bump BUMP in a horizontal direction (that is, a direction vertical to the third direction DR3) may be smaller than the width (or a planar size corresponding thereto) of the blood pressure sensor BPS in the horizontal direction. In another embodiment, as shown in FIG. 3B, a width of the bump BUMP in the horizontal direction may be substantially the same as the width of the blood pressure sensor BPS in the horizontal direction. In other words, since the bump BUMP has a relatively large modulus and a size substantially equal to or less than a size of the blood pressure sensor BPS and overlaps the blood pressure sensor BPS in the sensing area SA, the bump BUMP may concentrate the pressure applied to the sensing area SA on the blood pressure sensor BPS, particularly, the pressure sensor PS by preventing distribution of the pressure over a larger area than that to which the force is applied.

The bracket BRK may be disposed under the blood pressure sensor BPS. The bracket BRK may accommodate the window WIN, the display panel DP, the bump BUMP, and the blood pressure sensor BPS. A lower surface of the blood pressure sensor BPS may contact the bracket BRK, and the bracket BRK may support the blood pressure sensor BPS. Therefore, when the sensing area SA is pressurized, as described with reference to FIG. 5B, the pressure sensor PS of the blood pressure sensor BPS is deformed, and thus the pressure may be sensed. In some embodiments, an adhesive layer (that is, a layer including an adhesive material) may be disposed between the bracket BRK and the blood pressure sensor BPS, and the bracket BRK and the blood pressure sensor BPS may be combined through the adhesive layer.

As described with reference to FIG. 3A, FIG. 3B, FIG. 4, FIG. 5A, FIG. 5B, FIG. 6A, and FIG. 6B, the display device DD may include the bump BUMP overlapping the blood pressure sensor BPS (or pressure sensor PS), and may concentrate the pressure applied to the sensing area SA through the bump BUMP on the blood pressure sensor BPS. Accordingly, the pressure applied to the sensing area SA through the blood pressure sensor BPS may be more accurately measured, and thus the blood pressure may be more accurately measured.

FIG. 3A and FIG. 3B illustrate that the bump BUMP is disposed between the display panel DP and the blood pressure sensor BPS, but embodiments are not limited thereto. Another arrangement of the bump BUMP will be described later with reference to FIG. 10A to FIG. 10E.

Figure 7:
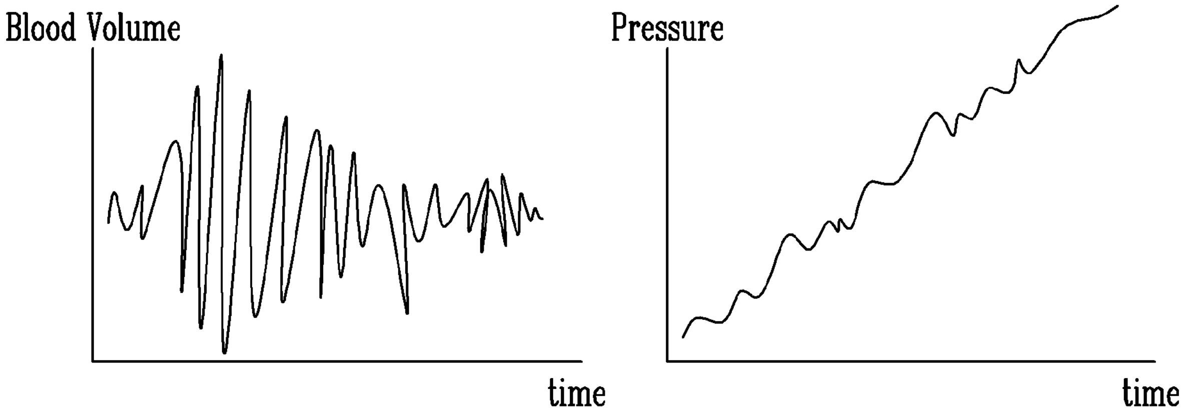
FIG. 7 illustrates graphs of blood volume and pressure of a portion of a user's body in contact with the display device of FIG. 1.

FIG. 7 illustrates graphs of blood volume and pressure of a portion of a user's body in contact with the display device of FIG. 1.

Referring to FIG. 1, FIG. 5A, FIG. 6A, FIG. 6B, and FIG. 7, the blood pressure detector DRV_BPS may calculate a blood pressure based on the first sensing signal SS1 (or pressure sensing signal) provided from the pressure sensor PS and the second sensing signal SS2 (or light sensing signal) provided from the photo sensor PPG.

As a volume of the blood vessel BV is changed, the amount of absorption of red blood cells (or hemoglobin HB) for light may be changed. The blood pressure detector DRV_BPS may calculate blood volume based on intensity of reflected light, reflectance ratio, and light transmissivity of layers between the window WIN to the bump BUMP. As shown in FIG. 7, the blood volume may oscillate in response to a change in the volume of blood vessel BV.

In addition, as shown in FIG. 7, while the user's finger presses the sensing area SA, the pressure on the sensing area SA may increase over time. As the pressure increases, blood gradually ceases to pass through the corresponding portion of the finger (that is, the portion pressing the sensing area SA). Accordingly, as shown in FIG. 7, as the pressure increases over time, the blood volume (or an amplitude of the blood volume) may decrease.

The blood pressure detector DRV_BPS may calculate blood pressure based on the change in blood volume according to pressure. For example, the blood pressure detector DRV_BPS may calculate blood pressure by applying the change in blood volume according to pressure to a predetermined blood pressure inference algorithm.

Figure 8A:
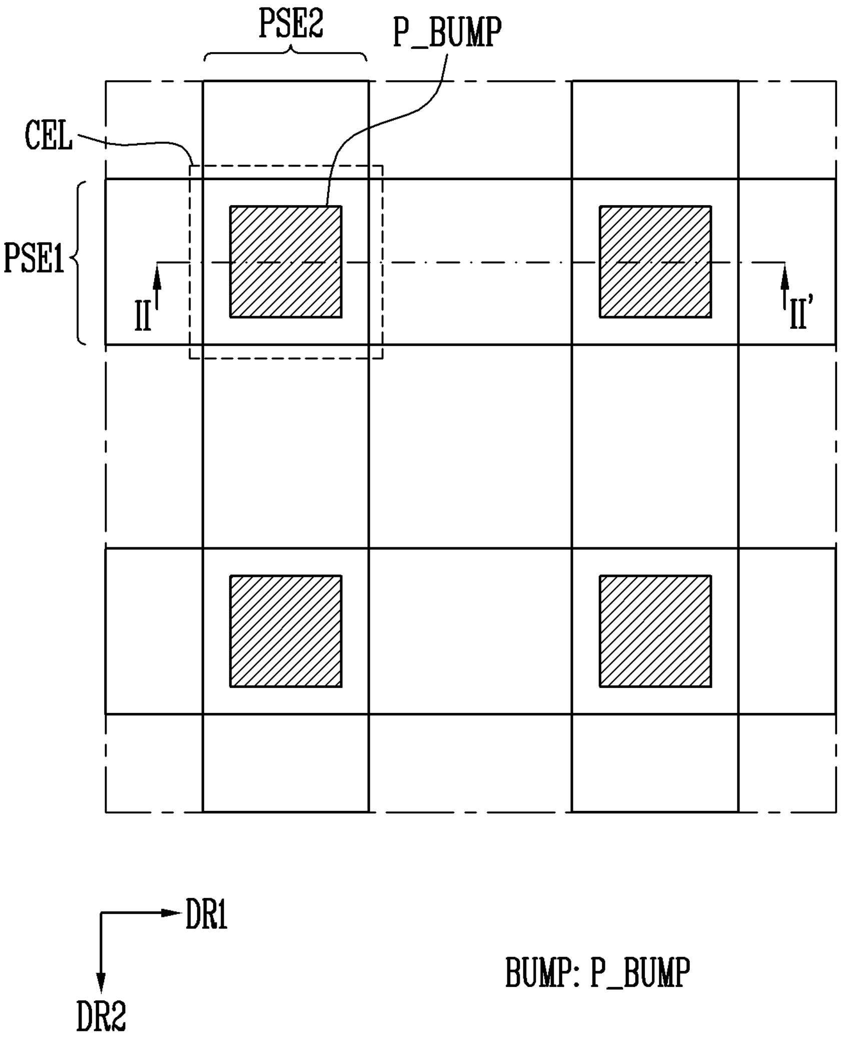
FIG. 8A is an enlarged plan view of an embodiment of the bump of FIG. 3A in a portion of the sensing area.
Figure 8B:
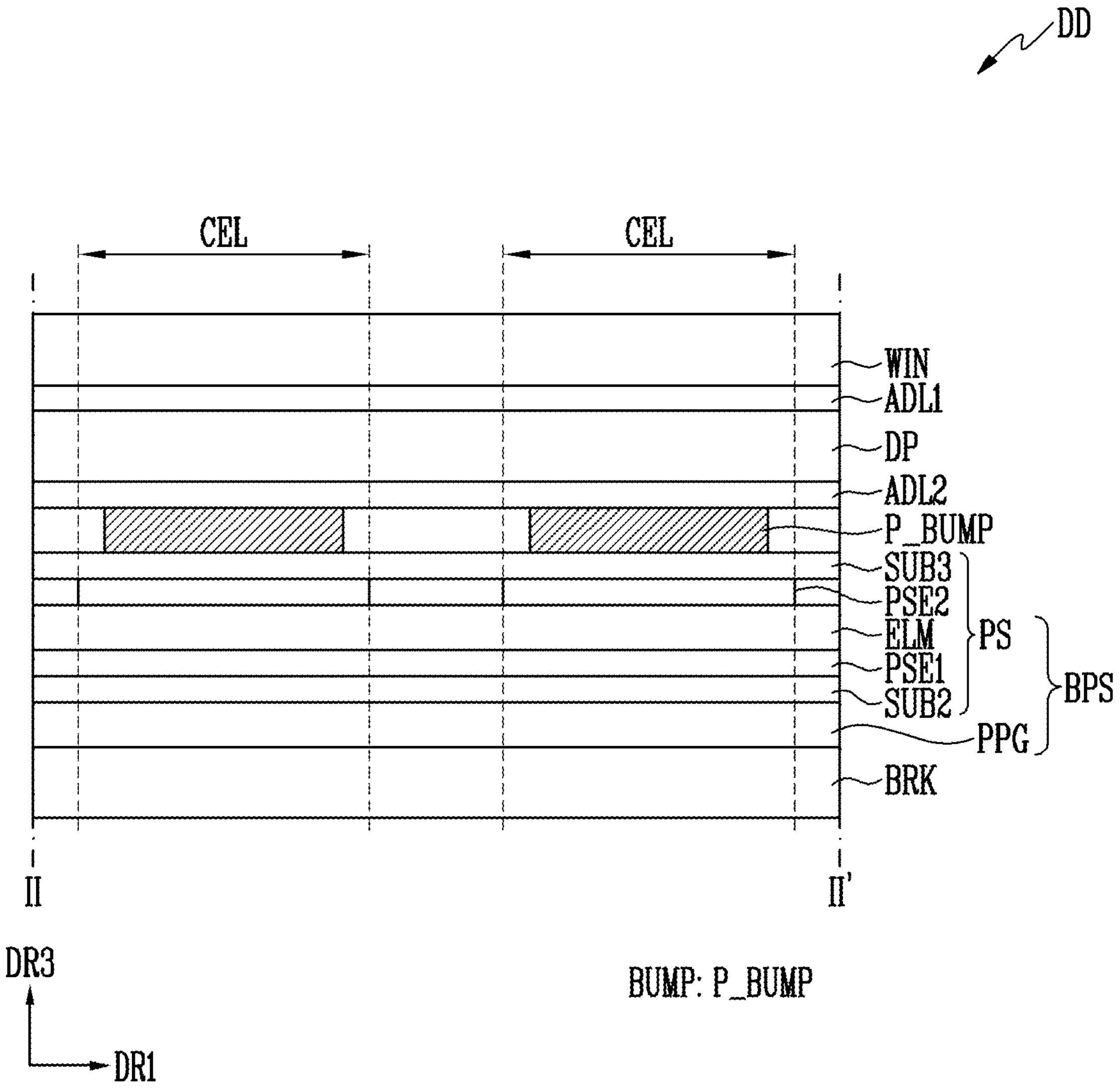
FIG. 8B and FIG. 8C are cross-sectional views of other embodiments of a display device taken along line II-II' of FIG. 8A.
Figure 8C:
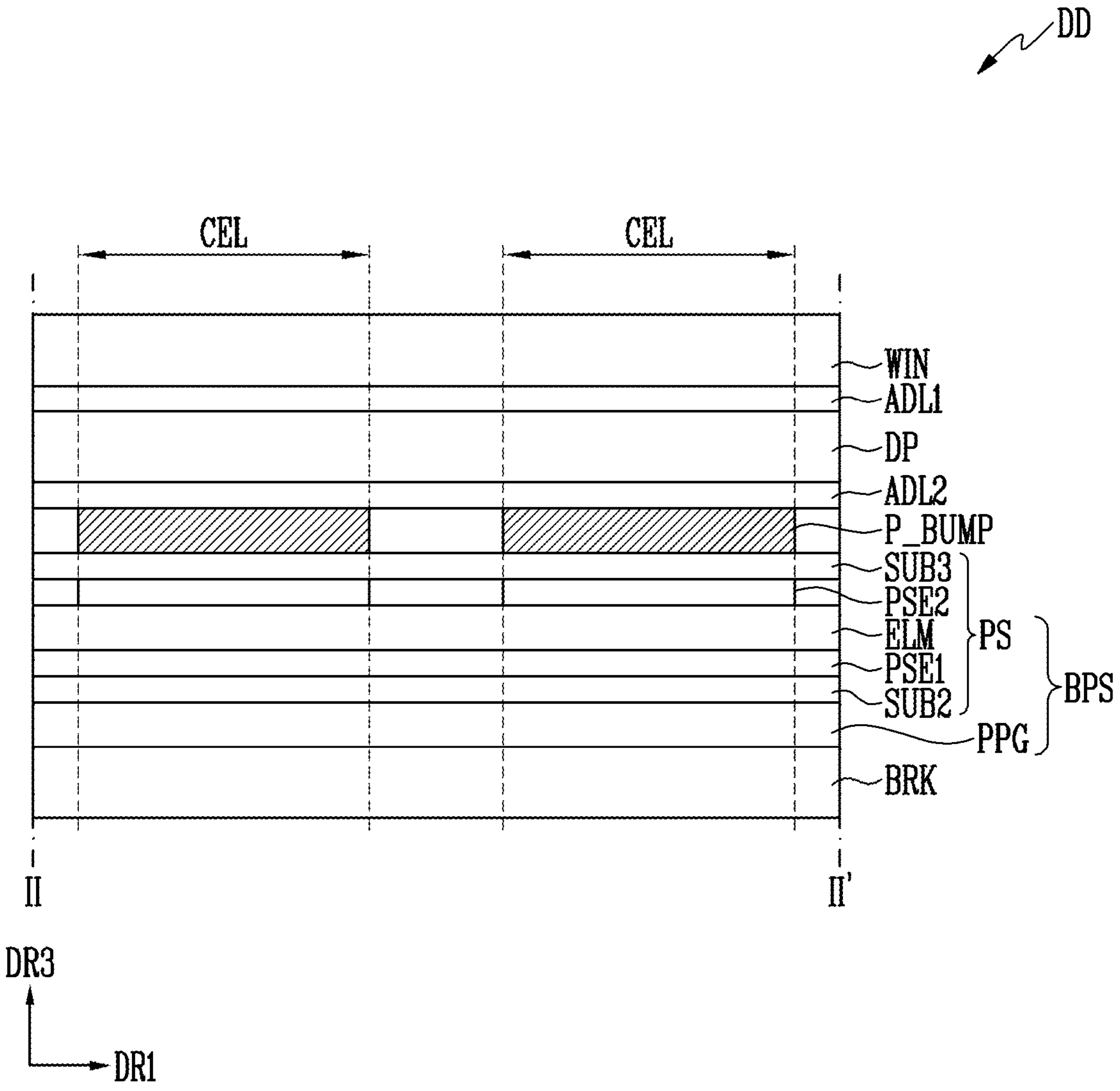
Figure 8D:
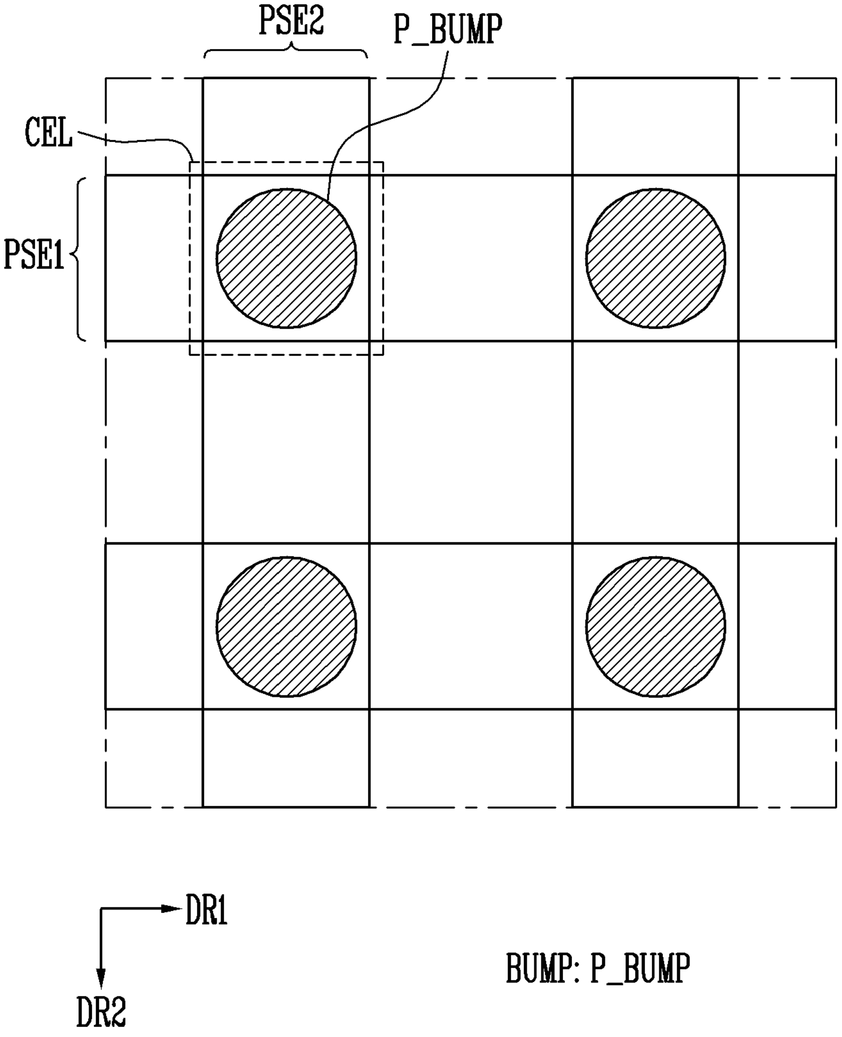
FIG. 8D is an enlarged plan view of another embodiment of the bump of FIG. 3A in a portion of the sensing area.

FIG. 8A is an enlarged plan view of an embodiment of the bump of FIG. 3A in a portion of the sensing area. FIG. 8A schematically illustrates the display device DD based on the pressure sensor PS and the bump BUMP. FIG. 8B and FIG. 8C are cross-sectional views of other embodiments of a display device taken along line II-II' of FIG. 8A. FIG. 8D is an enlarged plan view of another embodiment of the bump of FIG. 3A in a portion of the sensing area.

Referring to FIG. 1, FIG. 5A, FIG. 6A, FIG. 8A, FIG. 8B, FIG. 8C, and FIG. 8D, a pressure sensor PS including first electrodes PSE1 and second electrodes PSE2 may be substantially same as or similar to the pressure sensor PS including the first electrodes PSE1 and the second electrodes PSE2 described above with reference to FIG. 5A and FIG. 5B. In addition, a display panel DP, a window WIN, a photo sensor PPG, and a bracket BRK may be substantially the same as or similar to the display panel DP, the window WIN, the photo sensor PPG, and the bracket BRK described above with reference to FIG. 3A, respectively. Therefore, repetitive description will not be repeated to avoid redundancy.

In some embodiments, the bump BUMP may include bump patterns P_BUMP spaced apart from each other in a plan view.

As described above with reference to FIG. 3A, the bump patterns P_BUMP may include a material having a relatively large modulus. That is, the bump patterns P_BUMP may include a material that does not deform by repeated pressing. In an embodiment, the bump patterns P_BUMP may be made of a metallic material such as copper or aluminum, or a conductive material. In another embodiment, the bump patterns P_BUMP may be made of a polymer resin such as an epoxy resin or an acryl resin.

In an embodiment, the bump patterns P_BUMP may be formed on a carrier substrate, and may be attached to a lower surface of the display panel DP through the second adhesive layer ADL2. After the bump patterns P_BUMP are attached to the lower surface of the display panel DP, the carrier substrate may be removed.

The bump patterns P_BUMP may overlap areas (that is, the sensing cells CEL) in which the first electrodes PSE1 and the second electrodes PSE2 of the pressure sensor PS overlap in a plan view, respectively. For example, the bump pattern P_BUMP may have a size of about 1 mm by 1 mm.

In some embodiments, the planar size of each of the bump patterns P_BUMP may be smaller than or substantially equal to a planar size of each of the sensing cells CEL. In an embodiment, as shown in FIG. 8A and FIG. 8B, the planar size of each of the bump patterns P_BUMP may be smaller than that of each of the sensing cells CEL. In another embodiment, as shown in FIG. 8C, the planar size of each of the bump patterns P_BUMP may be substantially the same as that of each of the sensing cells CEL. The sensing cells CEL formed in each of the sensing cells CEL may independently sense the pressure of the corresponding position, and the bump patterns P_BUMP respectively overlapping the sensing cells CEL may concentrate the pressure applied to the corresponding sensing cell CEL on the corresponding sensing cell CEL.

When the bump BUMP is integrally configured, the pressure applied to the bump BUMP may be transferred to the entire area of the pressure sensor PS by the bump BUMP or evenly distributed to the pressure sensor PS. When the bump BUMP is relatively large, pressure may be distributed on the entire of the sensing area SA by the bump BUMP. In contrast, when the bump BUMP includes the bump patterns P_BUMP corresponding to respective sensing cells CEL, pressure may not be distributed and may be concentrated on each of the sensing cells CEL, which are the smallest units of pressure sensing. Accordingly, the pressure applied to the sensing area SA may be more accurately measured, and thus the blood pressure may be more accurately measured.

FIG. 8A illustrates that each of the bump patterns P_BUMP has a generally quadrangular planar shape, but the bump patterns P_BUMP are not limited thereto. For example, as shown in FIG. 8D, each of the bump patterns P_BUMP may have a generally circular planar shape. In addition, a hole or an opening may be formed in each of the bump patterns P_BUMP. Various shapes of the bump pattern P_BUMP will be described later with reference to FIG. 15A to FIG. 15D.

Figure 9:
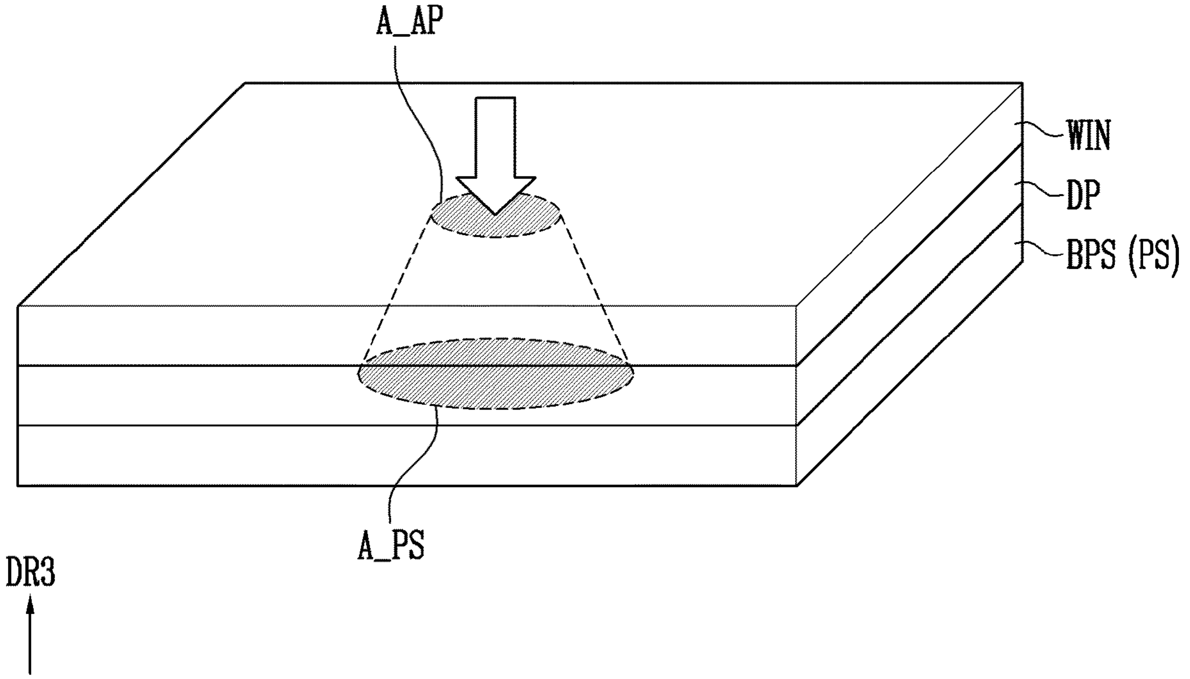
FIG. 9 is a perspective view of a comparative example of a display device.

FIG. 9 is a perspective view of a comparative example of a display device.

Referring to FIG. 3A and FIG. 9, the display device according to the comparative example may not include bump BUMP.

When the window WIN is pressurized, pressure propagation may be caused by the stacked structure of an upper portion of the blood pressure sensor BPS (or pressure sensor PS), such as the window WIN and the display panel DP. Accordingly, the pressure sensing area A_PS in which the pressure is sensed in the blood pressure sensor BPS may be larger than an actual pressurized area A_AP to which an actual pressure is applied.

Particularly, the pressure required for calculating the blood pressure is defined as the pressurized area to which the force is applied with respect to the applied force (that is, the pressure value sensed by the pressure sensor PS) (that is, pressure=force/area), and in this time, while the pressure sensing area A_PS is measured differently from the actual pressurized area A_AP, the pressurized area may not be accurately calculated.

The display device DD (see FIG. 3A and FIG. 8B) according to the illustrated embodiments may concentrate pressure on the actual pressurized area A_AP by using the bump BUMP. As the pressurized area is more accurately calculated, the blood pressure may be more accurately calculated.

FIG. 10A to FIG. 10E are cross-sectional views of still other embodiments of a display device taken along line I-I' of FIG. 1. FIG. 10A to FIG. 10E illustrate drawings corresponding to FIG. 3A.

Referring to FIG. 3A and FIG. 10A to FIG. 10E, except for the position of the bump BUMP, display devices DD_1, DD_2, DD_3, DD_4, and DD_5 shown in FIG. 10A to FIG. 10E may be substantially the same as or similar to the display device DD of FIG. 3A, respectively. Therefore, repetitive description will not be repeated to avoid redundancy. The bump BUMP of FIG. 8A to FIG. 8D may be provided in the embodiments of FIG. 10A to FIG. 10E.

Figure 10A:
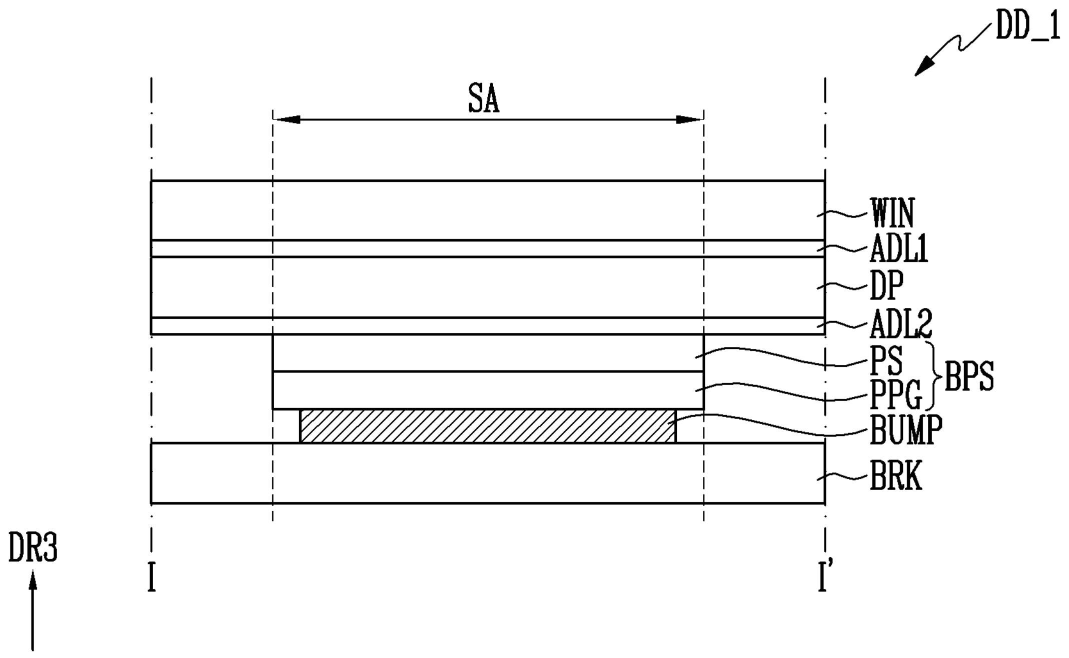
FIG. 10A to FIG. 10E are cross-sectional views of still other embodiments of a display device taken along line I-I' of FIG. 1.

As shown in FIG. 10A, the bump BUMP may be disposed between the blood pressure sensor BPS and the bracket BRK. The bump BUMP may be disposed under the photo sensor PPG.

The bump BUMP may be formed through coating or printing on a lower surface of the blood pressure sensor BPS (for example, a lower surface of the fourth substrate SUB4 shown in FIG. 6A), or it may be attached to the lower surface of the blood pressure sensor BPS through a separate adhesive layer.

Figure 10B:
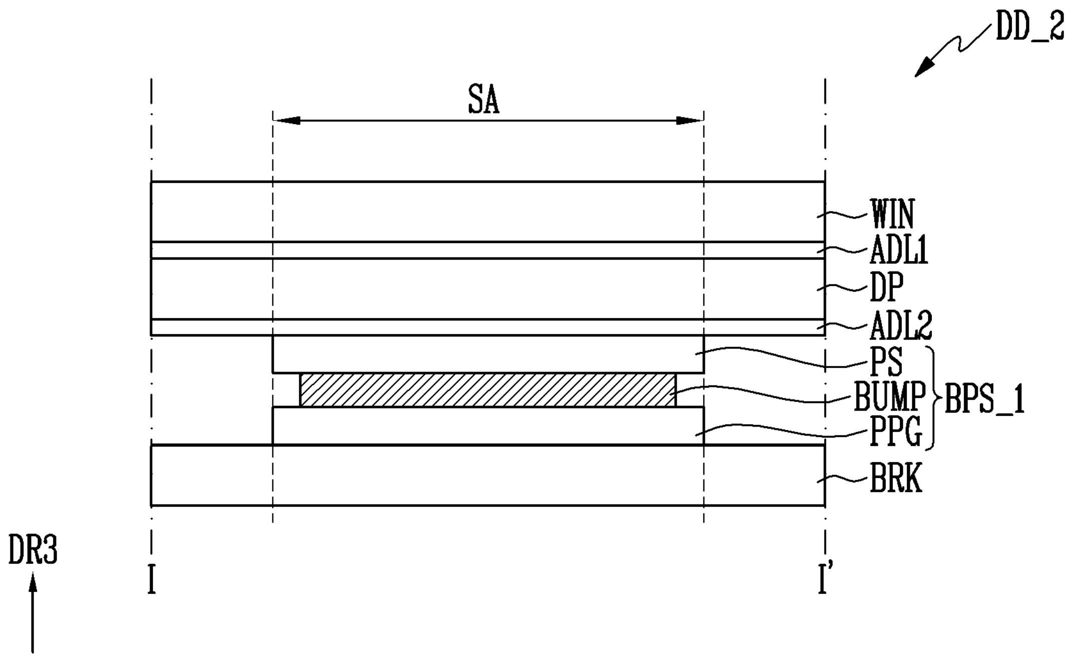

As shown in FIG. 10B, the bump BUMP may be included in a blood pressure sensor BPS_1. The bump BUMP may be disposed between the pressure sensor PS and the photo sensor PPG.

The bump BUMP may be formed through coating or printing on a lower surface of the pressure sensor PS (for example, a lower surface of the second substrate SUB2 shown in FIG. 5B), or it may be attached to the lower surface of the pressure sensor PS through a separate adhesive layer.

Figure 10C:
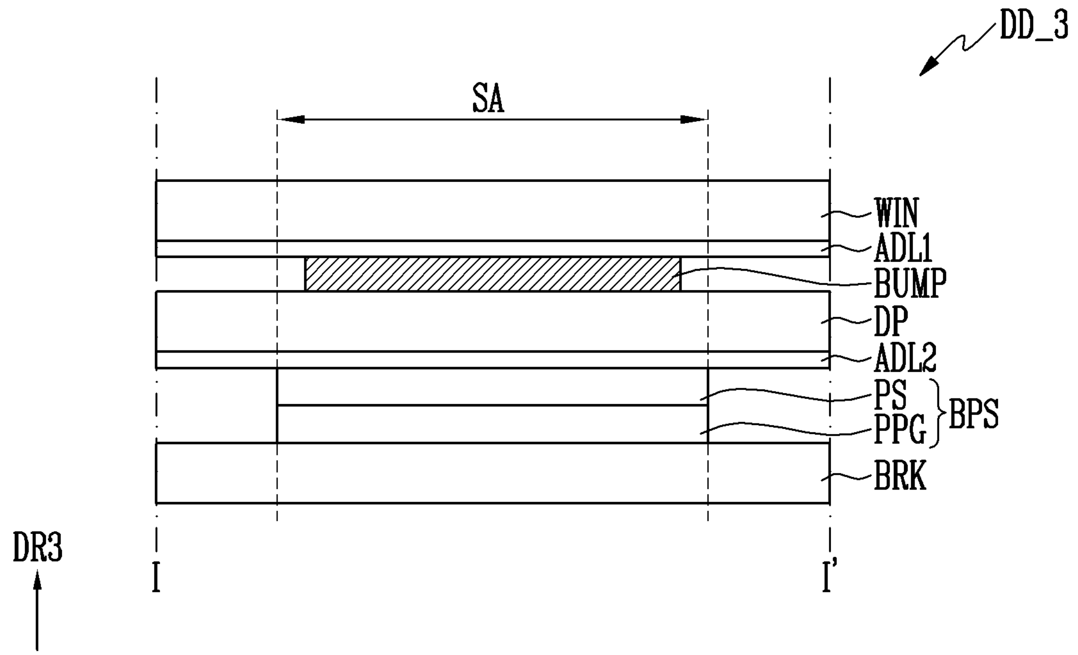

As shown in FIG. 10C, the bump BUMP may be disposed between the window WIN and the display panel DP. The bump BUMP may be disposed on the display panel DP. In this case, the bump BUMP may be made of a light transmissive material having a relatively large modulus.

The bump BUMP may be formed through coating or printing on an upper surface (for example, the first passivation layer PTL1 shown in FIG. 4) of the display panel DP, or it may be attached to the upper surface of the display panel DP through a separate adhesive layer.

Figure 10D:
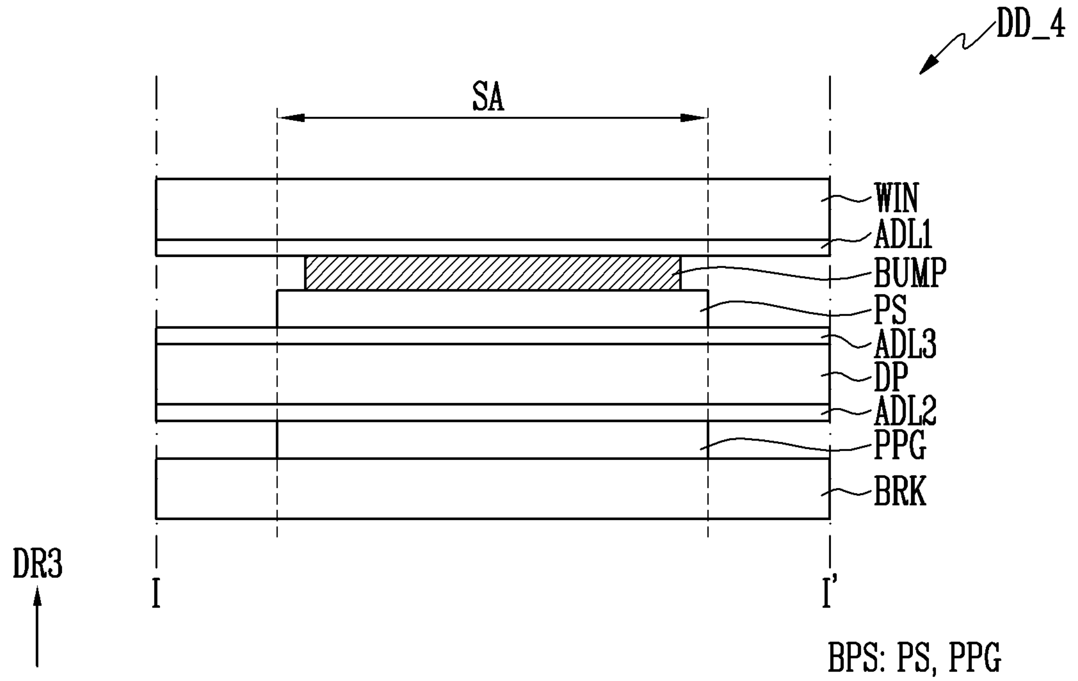

Referring to FIG. 10D, the pressure sensor PS may be disposed between the window WIN and the display panel DP. The pressure sensor PS may be attached to an upper surface of the display panel DP through a third adhesive layer ADL3. However, embodiments are not limited thereto, and for example, the pressure sensor PS may be directly formed on the display panel DP through a process subsequent to the manufacturing process of the display panel DP. In addition, the first electrode PSE1 (see FIG. 5A) and the second electrode PSE2 (see FIG. 5B) included in the pressure sensor PS may be made of a transparent conductive material, or they may have a mesh structure including a plurality of openings corresponding to and/or overlapping the pixel PXL (see FIG. 1).

In addition, the bump BUMP may be disposed between the window WIN and the pressure sensor PS. The bump BUMP may be formed through coating or printing on an upper surface of the pressure sensor PS, and may be attached to a lower surface of the window WIN by the first adhesive layer ADL1.

Since the pressure sensor PS and the bump BUMP are disposed closer to the window WIN, the actual pressurized area A_AP shown in FIG. 9 may be more accurately measured, and thus the blood pressure may be more accurately calculated.

Figure 10E:
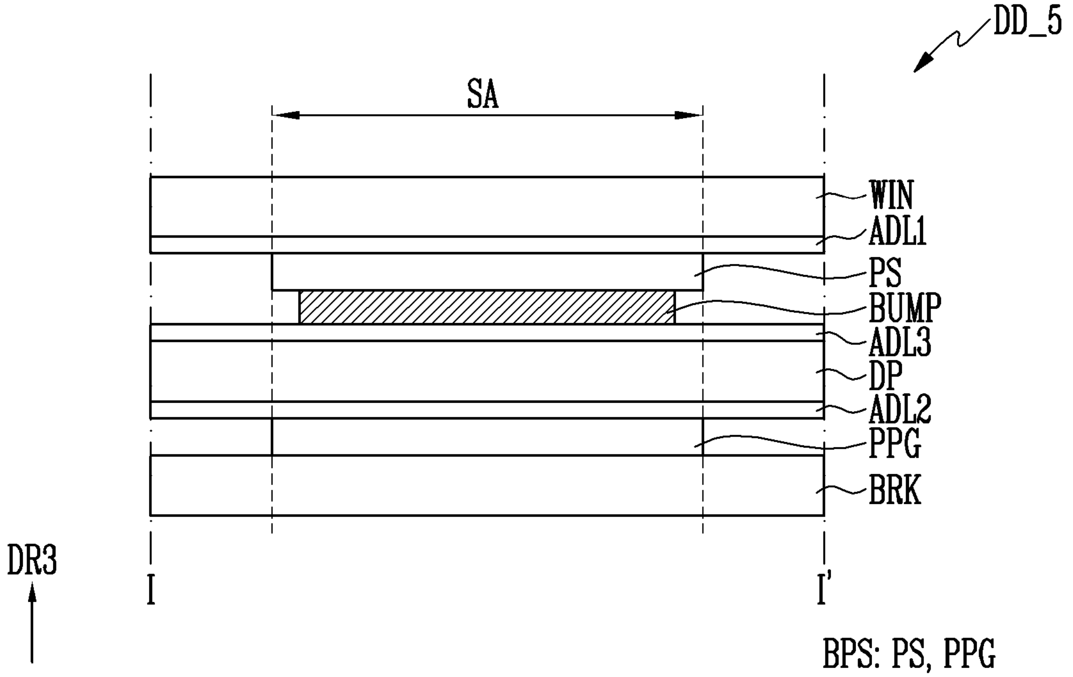

Referring to FIG. 10E, the pressure sensor PS may be disposed between the window WIN and the display panel DP. The pressure sensor PS may be attached to a lower surface of the window WIN through the first adhesive layer ADL1.

In addition, the bump BUMP may be disposed between the pressure sensor PS and the display panel DP. The bump BUMP may be formed through coating or printing on a lower surface of the pressure sensor PS, and can be attached to an upper surface of the display panel DP by the third adhesive layer ADL3.

As described with reference to FIG. 10A to FIG. 10E, the bump BUMP may be disposed in a number of positions between the window WIN, the display panel DP, and the blood pressure sensor BPS, overlapping the pressure sensor PS in the sensing area SA.

Figure 11:
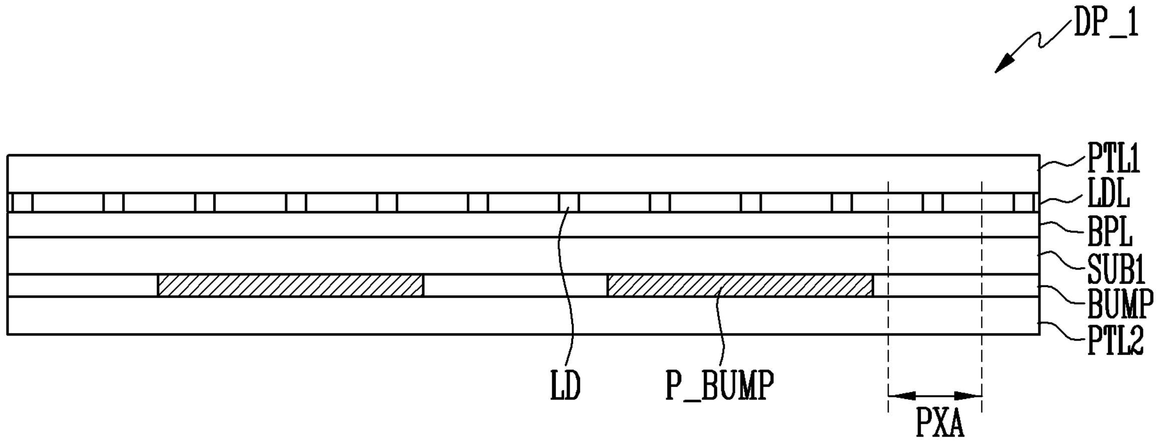
FIG. 11 is a cross-sectional view of another embodiment of a display panel.

FIG. 11 is a cross-sectional view of another embodiment of a display panel.

Referring to FIG. 4, FIG. 8A, and FIG. 11, a display panel DP_1 may further include the bump BUMP and a second passivation layer PTL2. Except for the bump BUMP and the second passivation layer PTL2, since the display panel DP_1 of FIG. 11 is substantially the same as or similar to the display panel DP of FIG. 4, redundant descriptions will not be repeated to avoid redundancy.

The second passivation layer PTL2 may be disposed under the first substrate SUB1. The second passivation layer PTL2 blocks oxygen and moisture from being introduced from the outside, and may be formed as a single layer or multilayer. The second passivation layer PTL2 may be formed in a film form to further secure flexibility of the display panel DP_1.

The bump BUMP may be disposed between the first substrate SUB1 and the second passivation layer PTL2. As described above with reference to FIG. 8A, the bump BUMP may include a plurality of bump patterns P_BUMP.

In an embodiment, the bump BUMP may be formed on the second passivation layer PTL2. For example, the bump BUMP may be formed through coating or printing on an upper surface of the second passivation layer PTL2. After the bump BUMP is formed, the first substrate SUB1, the circuit element layer BPL, the light emitting element layer LDL, and the first passivation layer PTL1 may be sequentially stacked.

In another embodiment, the bump BUMP may be formed on a lower surface of the first substrate SUB1. After the bump BUMP is formed, the second passivation layer PTL2 may be formed under the bump BUMP.

As described above with reference to FIG. 11, the bump BUMP may be provided inside the display panel DP. In this manner, as will be described later, in case where the display panel DP_1 includes an optical hole so as to improve transmittance of reflected light for the photo sensor PPG, the bump patterns P_BUMP that do not overlap the optical hole may be more easily formed through the manufacturing process of the display panel DP.

Figure 12A:
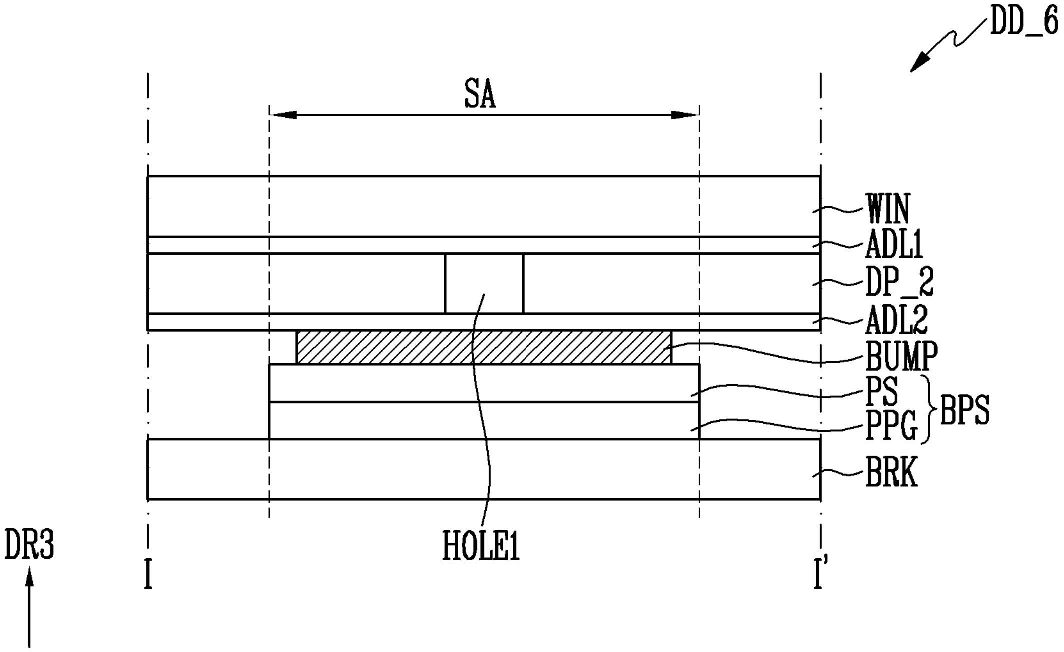
FIG. 12A is a cross-sectional view of yet another embodiment of a display device taken along line I-I' of FIG. 1.
Figure 12B:
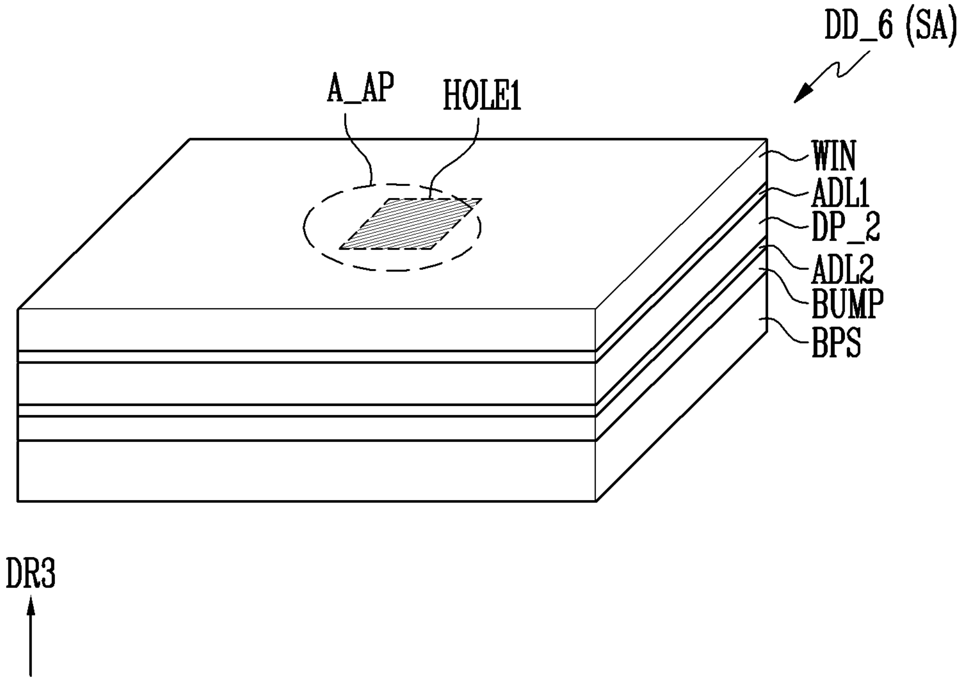
FIG. 12B is a perspective view of the display device of FIG. 12A.
Figure 12C:
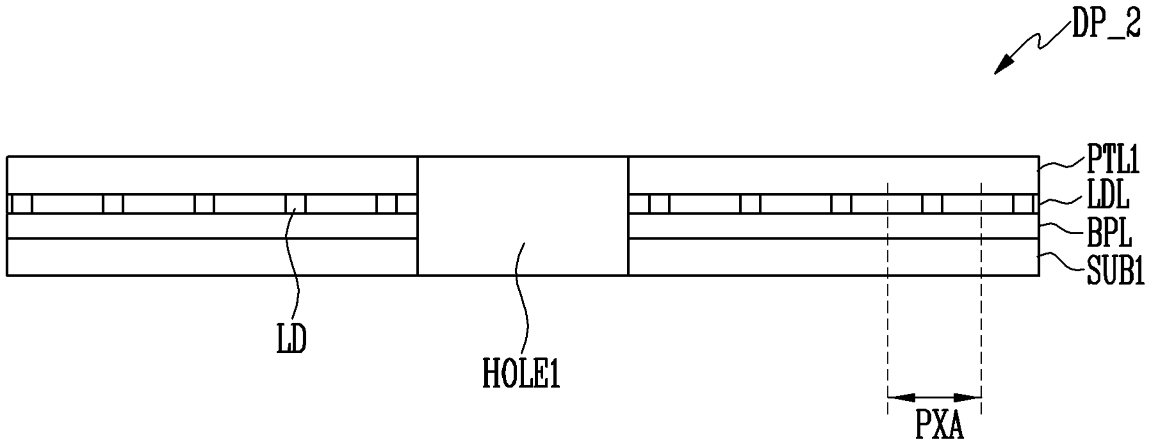
FIG. 12C is a cross-sectional view of an embodiment of the display panel of FIG. 12A.

FIG. 12A is a cross-sectional view of yet another embodiment of a display device taken along line I-I' of FIG. 1. FIG. 12B is a perspective view of the display device of FIG. 12A. FIG. 12C is a cross-sectional view of an embodiment of the display panel of FIG. 12A.

Referring to FIG. 1, FIG. 3A, FIG. 12A, FIG. 12B, and FIG. 12C, except for a display panel DP_2, a display device DD_6 of FIG. 12A may be substantially the same as or similar to the display device DD of FIG. 3A. In addition, except for a first hole HOLE1, the display panel DP_2 of FIG. 12C may be substantially the same as or similar to the display panel DP of FIG. 4. Therefore, repetitive descriptions will not be repeated to avoid redundancy.

The first hole HOLE1 exposing a lower component may be formed in the display panel DP_2.

The first hole HOLE1 may penetrate the first substrate SUB1, the circuit element layer BPL, the light emitting element layer LDL, and the first passivation layer PTL1 of the display panel DP_2, in the sensing area SA. The first hole HOLE1 may form a light path for the photo sensor PPG in the blood pressure sensor BPS. That is, the first hole HOLE1 is provided to increase transmittance of reflected light incident on the photo sensor PPG through the window WIN and the display panel DP_2.

In an embodiment, no material may be filled in the first hole HOLE1. That is, no solid material is filled in the first hole HOLE1, and air may exist.

In another embodiment, a color filter material may be filled in the first hole HOLE1. For example, when the photo sensor PPG uses green light, a color filter material that selectively transmits only green light may be filled in the first hole HOLE1. As another example, when the photo sensor PPG uses infrared rays, a material with high transmittance for infrared rays, for example, germanium, silicon, zinc selenide (ZnSe), silicon dioxide SiO2, polyethylene, polystyrene, or the like may be provided in the first hole HOLE1. It is possible to improve reliability of blood pressure (or blood flow) measurement by improving selectivity for a wavelength of light used in the photo sensor PPG.

In another embodiment, as an optical system for condensing light in the first hole HOLE1, silicon, an optical fiber, and the like may be disposed. For example, at least one optical fiber may be disposed in the first hole HOLE1. The optical fiber may include a core having a relatively high refractive index, and a cladding that surrounds the core and has a lower refractive index than the core. That is, an optical system using a refractive index difference may be provided in the first hole HOLE1.

In some embodiments, the diameter of the first hole HOLE1 may be several μm to several mm. According to the design of the photo sensor PPG, the diameter of the first hole HOLE1 may be variously set.

FIG. 12A, FIG. 12B, and FIG. 12C illustrate that only one first hole HOLE1 is formed in the display panel DP_2, but the display panel DP_2 is not limited thereto. For example, the display panel DP_2 may include a plurality of holes spaced apart from each other in the sensing area SA. This will be described later with reference to FIG. 14A.

FIG. 12B illustrates that the first hole HOLE1 has a generally quadrangular planar shape, but this is, and the first hole HOLE1 is not limited thereto. For example, the first hole HOLE1 may have one of various planar shapes such as a circle, an ellipse, or a polygon.

In case where the first hole HOLE1 is formed in the display panel DP_2, pressure may not be effectively and efficiently transmitted from the window WIN to the pressure sensor PS in the blood pressure sensor BPS through the first hole HOLE1. Accordingly, compared with the display device DD (see FIG. 3A) including the display panel DP (see FIG. 4) in which the first hole HOLE1 is not formed, the pressure sensed by the pressure sensor PS may be varied. Particularly, if the bump BUMP are not provided, the pressure sensed by the pressure sensor PS may be varied according to the pressurized position (that is, a position of the actual pressurized area A_AP) with respect to a center of an area of the first hole HOLE1.

TABLE 1

| | Pressure [kPa] | | |
|---|---|---|---|
| Pressurized position | Hole O | Hole X | Reduction rate (%) |
| Center | 54.92 | 64.51 | 14.86 |
| Center - 1 mm | 54.79 | 64.52 | 15.08 |
| Center - 2 mm | 55.13 | 64.53 | 14.58 |
| Center - 3 mm | 55.63 | 64.47 | 13.70 |

Table 1 shows the pressure sensed by the pressure sensor PS according to the pressurized position with respect to the center of the area of the first hole HOLE1 in the display device in which the bump BUMP is not provided.

When the pressurized position coincides with the center of the area of the first hole HOLE1, a first pressure sensed in the display device DD_6 including the display panel DP_2 in which the first hole HOLE1 is formed is reduced by 14.86% compared to a second pressure sensed in the display device DD (see FIG. 3A) in which no hole is provided.

When the pressurized position is moved or shifted by about 1 mm from the center of the area of the first hole HOLE1, the first pressure sensed in the display device DD_6 including the display panel DP_2 in which the first hole HOLE1 is formed is reduced by 15.08% compared to a second pressure sensed in the display device DD (see FIG. 3A) in which no hole is provided. That is, compared to the case in which the pressurized position coincides with the center of the area of the first hole HOLE1, the reduction rate is changed. For reference, when the pressurized position moves from the center of the area of the first hole HOLE1, the second pressure is not substantially changed, but the first pressure may be changed.

When the pressurized position is shifted or moved by about 2 mm from the center of the area of the first hole HOLE1, the reduction rate (that is, the ratio of the difference between the first pressure and the second pressure based on the second pressure) is changed.

Since the first pressure sensed in the display device DD_6 including the display panel DP_2 in which the first hole HOLE1 is formed is reduced compared to the second pressure sensed in the display device DD (see FIG. 3A) in which no hole is provided, the first pressure should be compensated by the reduction rate. Also, since the reduction rate varies depending on a blood pressure measurement condition (that is, a position the user touches) there may be an error in the first pressure, and the blood pressure measurement and accuracy thereof may be lowered.

The display device DD_6 of the illustrated embodiment has the bump BUMP, thereby reducing an error for the first pressure.

TABLE 2

| Pressurized position | bump X | bump O |
|---|---|---|
| Center - 1 mm | 0.24% | 0.03% |
| Center - 2 mm | 0.37% | 0.05% |
| Center - 3 mm | 1.29% | 0.37% |

Table 2 shows errors of the first pressure sensed by the display device in which the bump BUMP is not provided and by the display device DD_6 in which the bump BUMP is provided. That is, Table 2 shows the errors of the first pressure depending on the pressurized position with respect to the center of the area of the first hole HOLE1.

In the case where the display device is not provided with the bump BUMP, errors of 0.24%, 0.37%, and 1.29% occur at the pressurized positions of about 1 mm, 2 mm, and 3 mm from the center of the area of the first hole HOLE1, and in the case where the display device DD_6 is provided with the bump BUMP, errors of 0.03%, 0.05%, and 0.37% may occur at the pressurized positions of about 1 mm, 2 mm, and 3 mm from the center of the area of the first hole HOLE1. That is, the display device DD_6 including the bump BUMP may significantly reduce the error rate of the measured pressure according to the pressurized position.

As described with reference to FIG. 12A to FIG. 12C, the display device DD_6 may include the display panel DP_2 in which the first hole HOLE1 is formed in the sensing area SA. Therefore, the amount of reflected light that transmits through the display panel DP_2 and is incident on the blood pressure sensor BPS (or the photo sensor PPG) may increase, the sensitivity of the photo sensor PPG may be improved, and the accuracy of blood pressure measurement may be improved. In addition, since the display device DD_6 includes the bump BUMP, it is possible to reduce an error of pressure sensed by the pressure sensor PS, and it is possible to prevent a decrease in accuracy of blood pressure measurement.

FIG. 12A and FIG. 12B illustrate that the bump BUMP is disposed between the display panel DP_2 and the blood pressure sensor BPS, but the position of the bump BUMP is not limited thereto. As described with reference to FIG. 10A to FIG. 10E, the bump BUMP may be disposed at various positions between the window WIN, the display panel DP, and the blood pressure sensor BPS as long as the bump BUMP overlaps the pressure sensor PS in the sensing area SA. That is, the display panel DP_2 of FIG. 12A to FIG. 12C may also be applied to the display devices DD_1 to DD_5 of FIG. 10A to FIG. 10E.

Figure 13A:
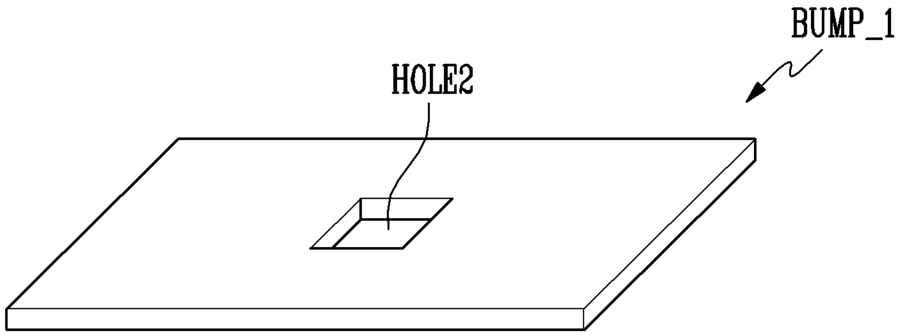
FIG. 13A is a perspective view of an embodiment of the bump of FIG. 12A.
Figure 13B:
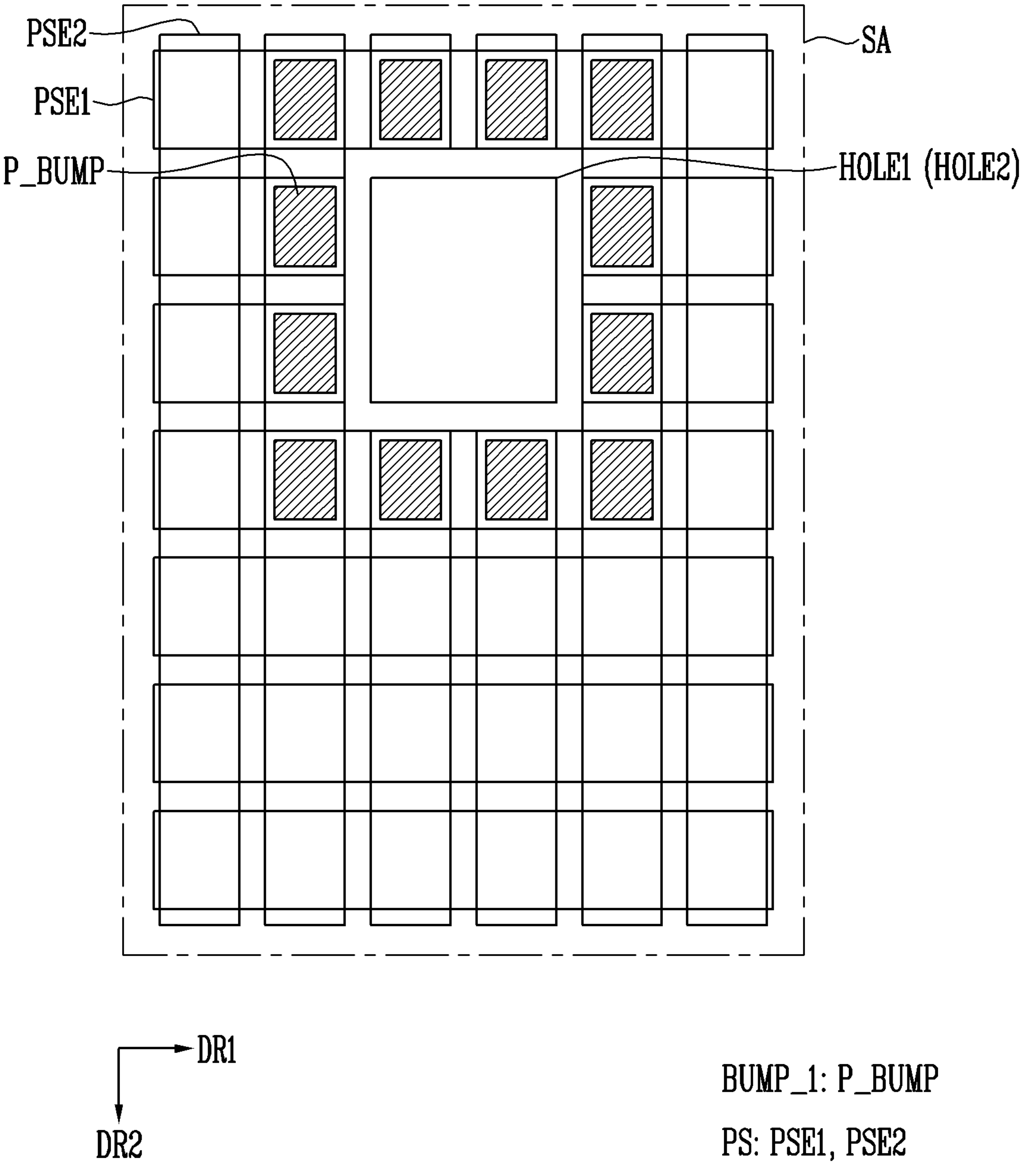
FIG. 13B to FIG. 13D are plan views of other embodiments of the bump of FIG. 12A.
Figure 13C:
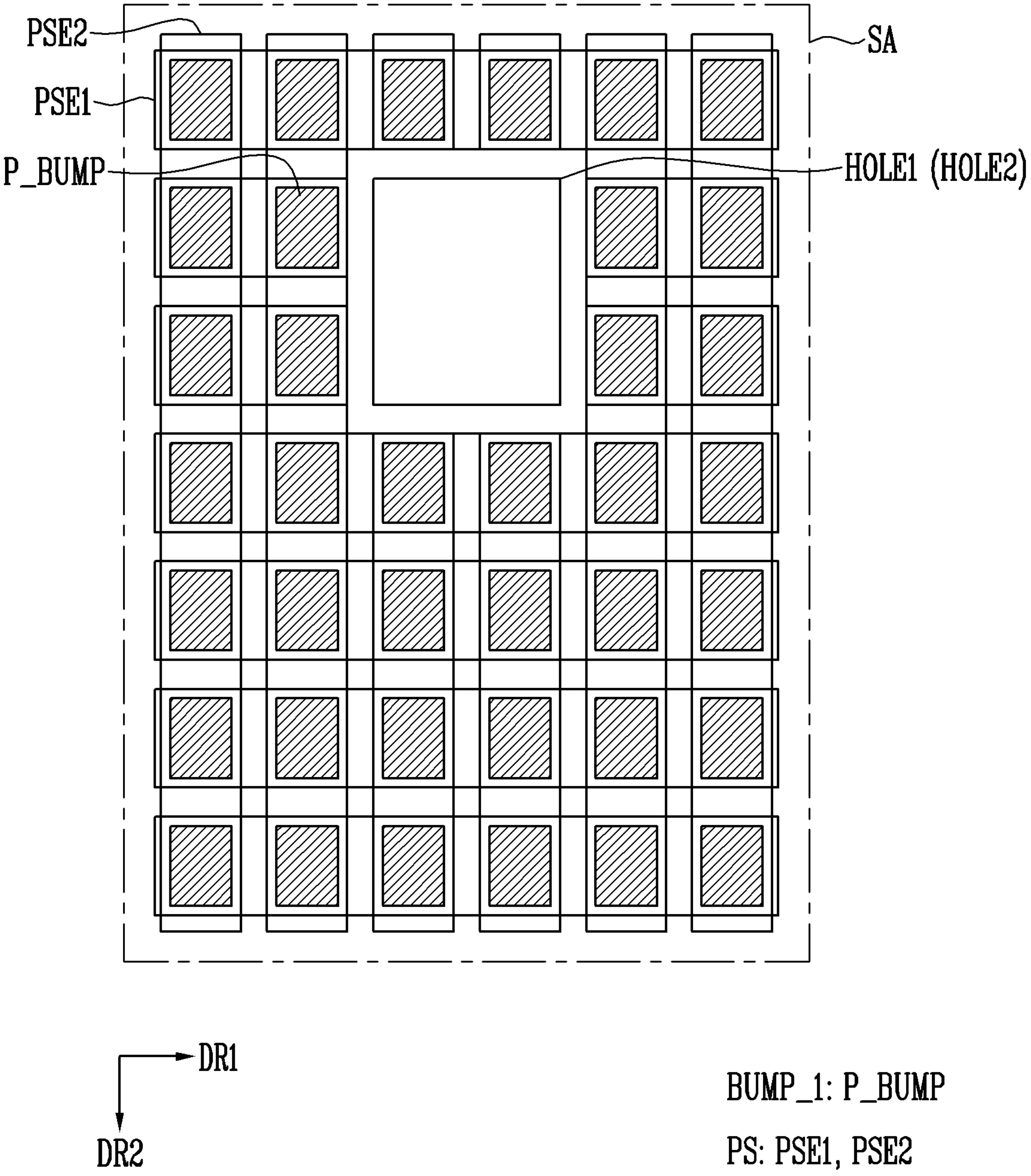
Figure 13D:
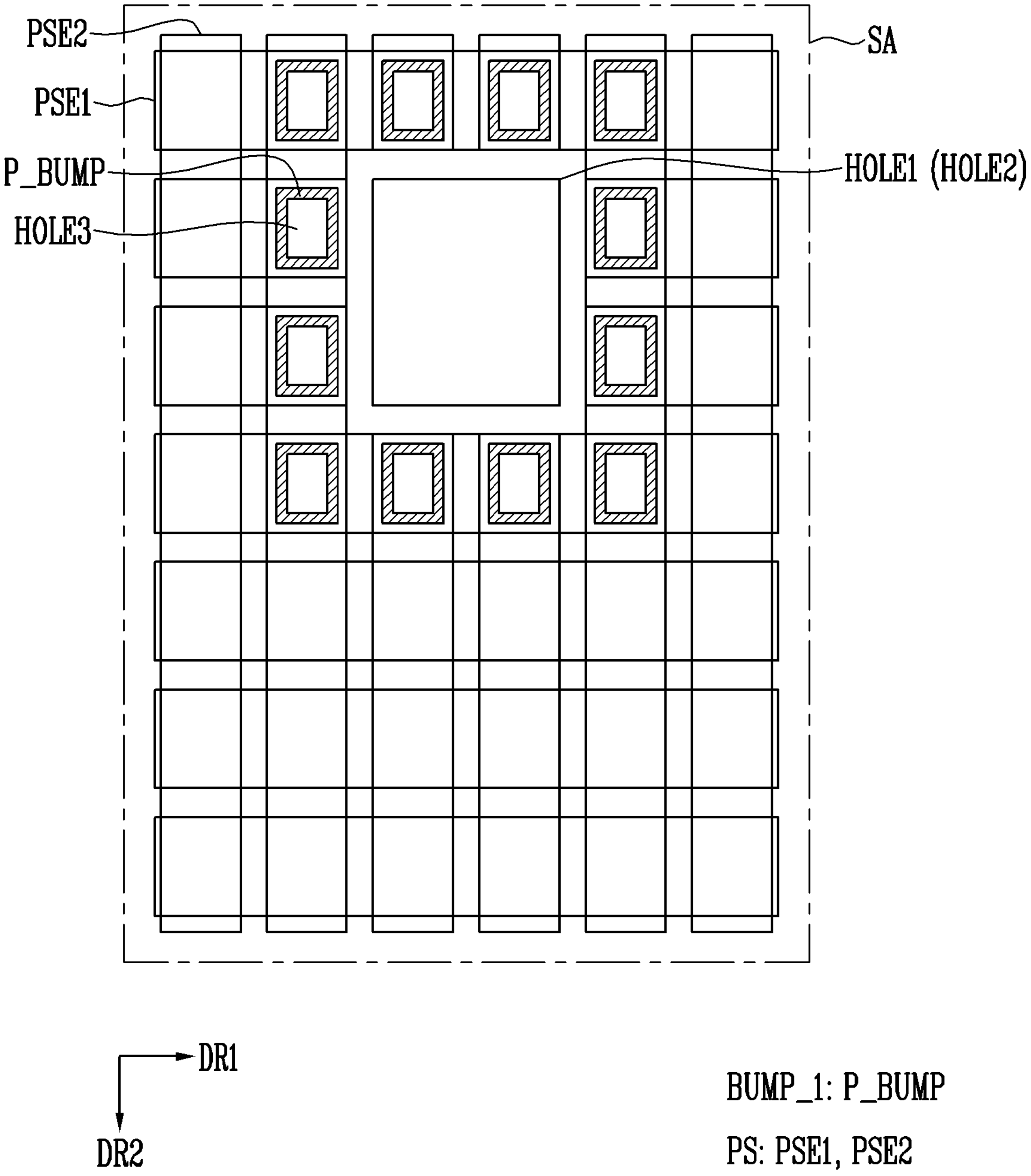

FIG. 13A is a perspective view of an embodiment of the bump of FIG. 12A. FIG. 13B to FIG. 13D are plan views of other embodiments of the bump of FIG. 12A. FIG. 13B, FIG. 13C, and FIG. 13D additionally illustrate the first electrodes PSE1 and the second electrode PSE2 of the pressure sensor PS to explain arrangement positions of the bump patterns P_BUMP.

Referring to FIG. 12A, FIG. 13A, FIG. 13B, FIG. 13C, and FIG. 13D, a second hole HOLE2 exposing a lower component may be formed in a bump BUMP_1. The second hole HOLE2 may penetrate through the bump BUMP_1. The second hole HOLE_2 may correspond to and/or overlap the first hole HOLE1 of the display panel DP_2. That is, the second hole HOLE2 in the display device DD_6 may be aligned with the first hole HOLE1. Therefore, the amount of reflected light that transmits through the display panel DP_2 and the bump BUMP_1 and is incident on the blood pressure sensor BPS (or the photo sensor PPG) may increase, the sensitivity of the photo sensor PPG may be improved, and the accuracy of blood pressure measurement may be improved.

A planar shape of the second hole HOLE2 may be substantially the same as that of the first hole HOLE1, but is not limited thereto, and for example, the planar shape of the second hole HOLE2 may be different from that of the first hole HOLE1.

As shown in FIG. 13B, the bump BUMP may include the bump patterns P_BUMP spaced apart from each other in a plan view. Since the bump patterns P_BUMP are substantially the same as or similar to the bump patterns P_BUMP described with reference to FIG. 8A, redundant descriptions will not be repeated to avoid redundancy.

In an embodiment, as shown in FIG. 13B, the bump patterns P_BUMP may be arranged along an edge of the second hole HOLE2. The bump patterns P_BUMP may be arranged in a line along the edge of the second hole HOLE2. However, embodiments are not limited thereto, and the bump patterns P_BUMP may be arranged in two or more lines along the edge of the second hole HOLE2 and have substantially the same width. In this case, even if the pressurized position described with reference to FIG. 12B (that is, the position of the actual pressurized area A_AP) moves in the first direction DR1 and/or second direction DR2, the pressure may be accurately sensed. That is, in order to prevent occurrence of an error due to the pressurized position, the bump patterns P_BUMP may have a substantially constant width as a whole and may be surround the second hole HOLE2.

In another embodiment, as shown in FIG. 13C, the bump patterns P_BUMP may be entirely arranged in the sensing area SA excluding the second hole HOLE2.

In some embodiments, as shown in FIG. 13D, a third hole HOLE3 may be formed in each of the bump patterns P_BUMP. As will be described later, in order to improve transmittance of light emitted from the light emitting portion LED in the photo sensor PPG or of reflected light corresponding to the light, the third hole HOLE3 may be formed in the bump pattern P_BUMP.

As described with reference to FIG. 13A to FIG. 13D, the second hole HOLE2 may be formed in the bump BUMP_1 corresponding to the first hole HOLE1 of the display panel DP_2. Therefore, the amount of reflected light that transmits through the display panel DP_2 and the bump BUMP_1 and is incident on the blood pressure sensor BPS (or the photo sensor PPG) may increase, the sensitivity of the photo sensor PPG may be improved, and the accuracy of blood pressure measurement may be improved.

Figure 14A:
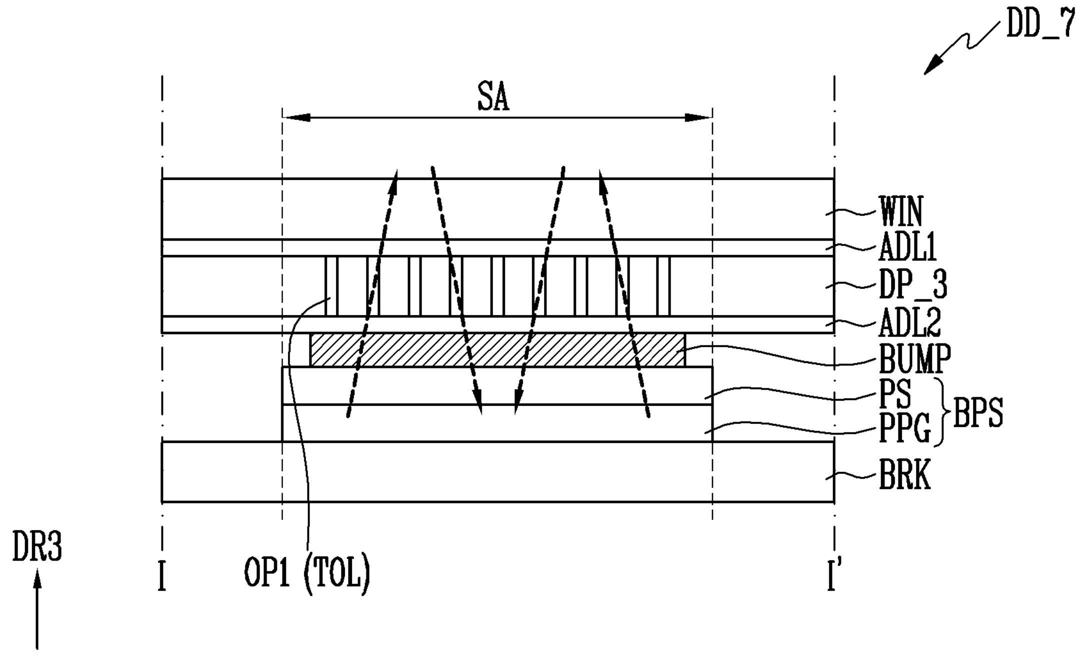
FIG. 14A is a cross-sectional view of yet still another embodiment of a display device taken along line I-I' of FIG. 1.
Figure 14B:
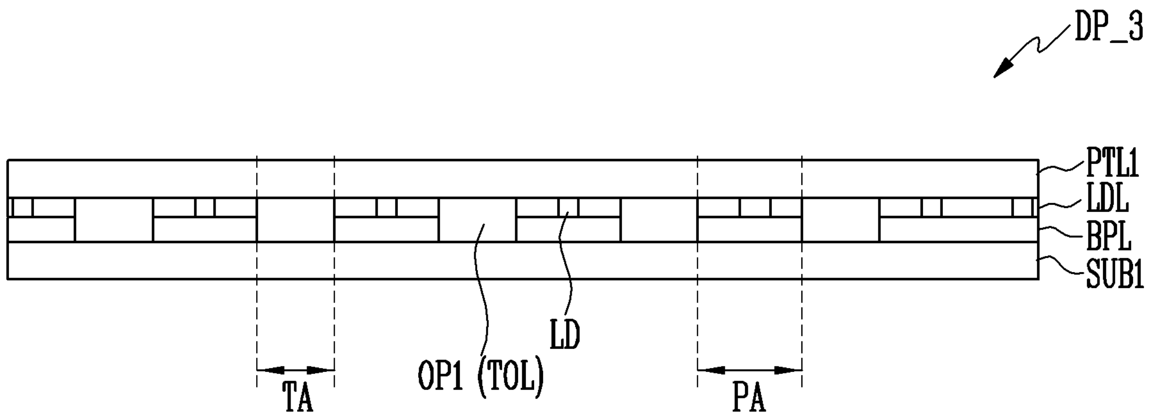
FIG. 14B is a cross-sectional view of an embodiment of the display panel of FIG. 14A.
Figure 14C:
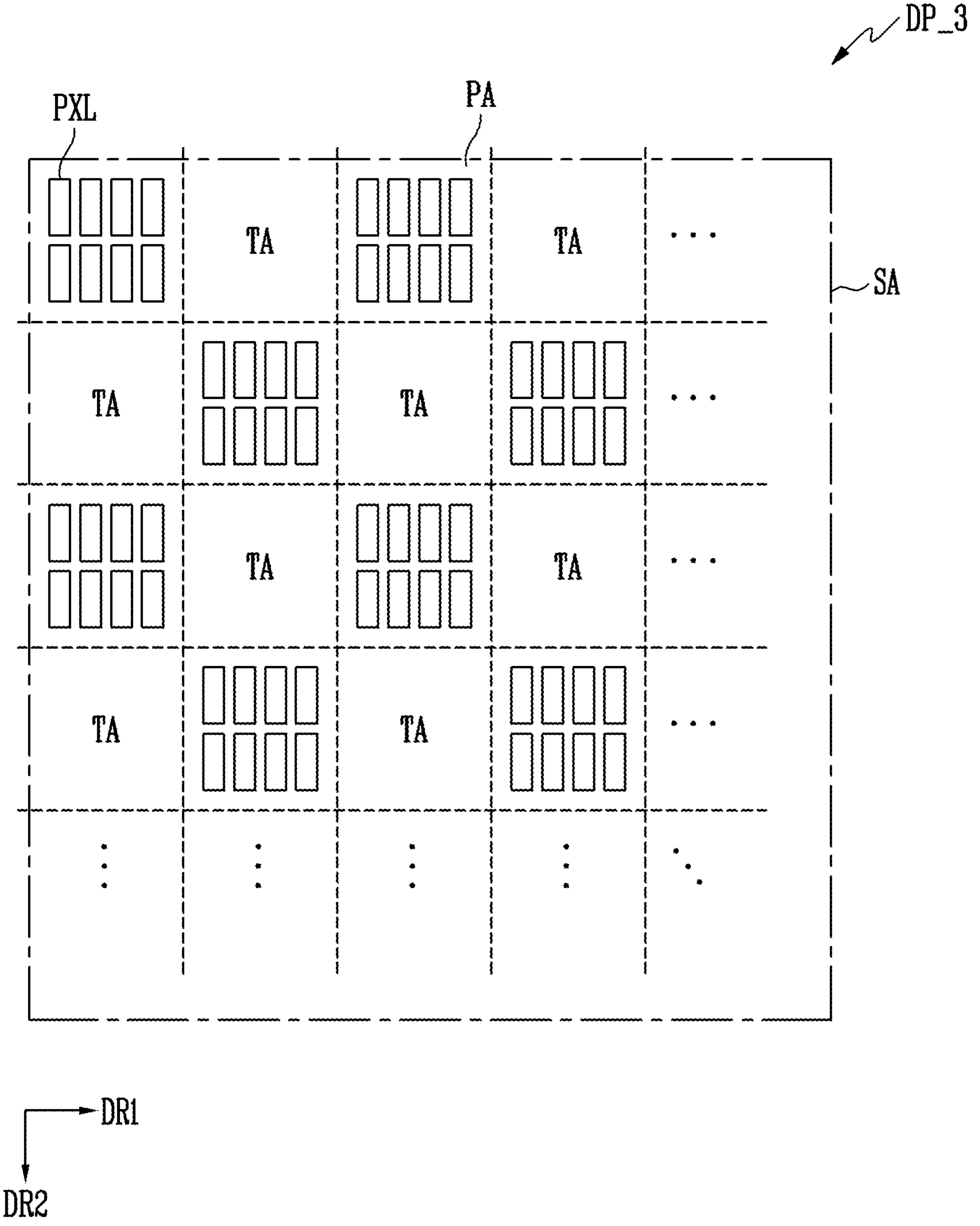
FIG. 14C is a plan view of an embodiment of the display panel of FIG. 14B.

FIG. 14A is a cross-sectional view of yet still another embodiment of a display device taken along line I-I' of FIG. 1. FIG. 14B is a cross-sectional view of an embodiment of the display panel of FIG. 14A. FIG. 14C is a plan view of an embodiment of the display panel of FIG. 14B.

Referring to FIG. 1, FIG. 3A, FIG. 14A, FIG. 14B, and FIG. 14C, except for a display panel DP_3, a display device DD_7 of FIG. 14A may be substantially the same as or similar to the display device DD of FIG. 3A. In addition, except for a first opening OP1, a display panel DP_3 of FIG. 14B may be substantially the same as or similar to the display panel DP of FIG. 4. Therefore, repetitive descriptions will not be repeated to avoid redundancy.

The first openings OP1 (or light paths, light transmissive paths) exposing a lower component may be formed in the display panel DP_3. The first openings OP1 may not overlap the light emitting elements LD and the conductive patterns.

As shown in FIG. 14B, the first openings OP may be formed in the circuit element layer BPL and the light emitting element layer LDL. Only a plurality of insulation layers is provided in the first openings OP1, and a conductive element (for example, a wire, an electrode of a transistor, a conductive pattern, an electrode of a light emitting element, etc.) may not be disposed therein. In addition, a material having relatively high light transmittance may be further disposed in the first openings OP1.

In an embodiment, a material having a refractive index different from that of the insulation layers may be disposed in the first openings OP1. For example, a transparent organic layer TOL having a refractive index greater than that of the insulation layers may be disposed in the first openings OP1. In this case, light emitted from the photo sensor PPG in the third direction DR3 may be totally reflected between the transparent organic layer and the insulation layers (that, at edges of the first openings OP1), and the amount of light emitted from the photo sensor PPG or received by the photo sensor PPG may increase, and sensitivity of the photo sensor PPG may be improved. For example, the transparent organic layer TOL may be formed as a single film including an acryl resin, an epoxy resin, a phenolic resin, a polyamide resin, a polyimide resin, and the like.

In another embodiment, a material having high transmittance with respect to infrared rays, for example, germanium, silicon, zinc selenide (ZnSe), silicon dioxide SiO2, polyethylene, polystyrene, or the like may be disposed in the first openings OP1.

The area in which the first opening OP1 is formed in the display panel DP_3 is defined as a transmissive area TA, and the area excluding the first opening OP1, that is, the area in which the light emitting element LD and the conductive patterns (or pixels PXL) are disposed may be defined as a pixel area PA.

In some embodiments, as shown in FIG. 14C, the pixel areas PA have a checkerboard shape in the sensing area SA, and they may be spaced apart from each other. For example, the pixel areas PA and the transmissive areas TA may be alternately arranged in areas partitioned by horizontal reference lines extending in the first direction DR1 and vertical reference lines extending in the second direction DR2. Each of the pixel areas PA may include a plurality of pixels PXL. FIG. 14C illustrates that each of the pixel areas PA includes eight pixels PXL, but this is, and for example, each of the pixel areas PA may include 2 to 7 pixels, or 9 or more pixels PXL, and the size of the pixel areas PA (or transmissive areas TA) may be variously set in consideration of the size of a bump pattern P_BUMP (see FIG. 15A) to be described later.

While FIG. 14C illustrates that the pixel areas PA and the transmissive areas TA are alternately arranged, embodiments are not limited thereto. For example, each of the transmissive areas TA may be disposed in an island shape, and each of the transmissive areas TA may be surrounded by the pixel areas PA.

As described with reference to FIG. 14A to FIG. 14C, the display device DD_7 may include the display panel DP_3 in which the first openings OP1 are formed in the sensing area SA. Accordingly, the amount of light emitted from the photo sensor PPG or received by the photo sensor PPG may increase, sensitivity of the photo sensor PPG may be improved, and accuracy of the blood pressure measurement may be improved.

FIG. 14A illustrate that the bump BUMP is disposed between the display panel DP_3 and the blood pressure sensor BPS, but the arrangement position of the bump BUMP is not limited thereto. As described with reference to FIG. 10A to FIG. 10E, the bump BUMP may be disposed in various positions between the window WIN, the display panel DP_3, and the blood pressure sensor BPS as long as the bump BUMP overlaps the pressure sensor PS in the sensing area SA. That is, the display panel DP_3 of FIG. 14A to FIG. 14C may also be applied to the display devices DD_1 to DD_5 of FIG. 10A to FIG. 10E.

FIG. 15A to FIG. 15D are plan views of embodiments of the bump of FIG. 14A including bump patterns arranged in association with the display panel of FIG. 14C. FIG. 15A to FIG. 15D additionally illustrate the transmissive areas TA and the pixel areas PA to explain the arrangement position of the bump patterns P_BUMP.

Referring to FIG. 8A, and FIG. 15A to FIG. 15D, the bump BUMP may include the bump patterns P_BUMP spaced apart from each other in a plan view. Since the bump patterns P_BUMP are substantially the same as or similar to the bump patterns P_BUMP described with reference to FIG. 8A, redundant descriptions will not be repeated to avoid redundancy. As described with reference to FIG. 8A, the bump patterns P_BUMP may respectively overlap the sensing cells CEL formed by overlapping the first electrodes PSE1 and the second electrodes PSE2 in a plan view.

Each of the bump patterns P_BUMP may have a size (or area) similar to that of the transmissive area TA or pixel area PA. For example, each of the bump patterns P_BUMP may have a size of about 1 to about 1.5 times that of the transmissive area TA or pixel area PA.

In other words, the transmissive area TA or pixel area PA may be formed to have a size similar to that of the bump pattern P_BUMP.

Figure 15A:
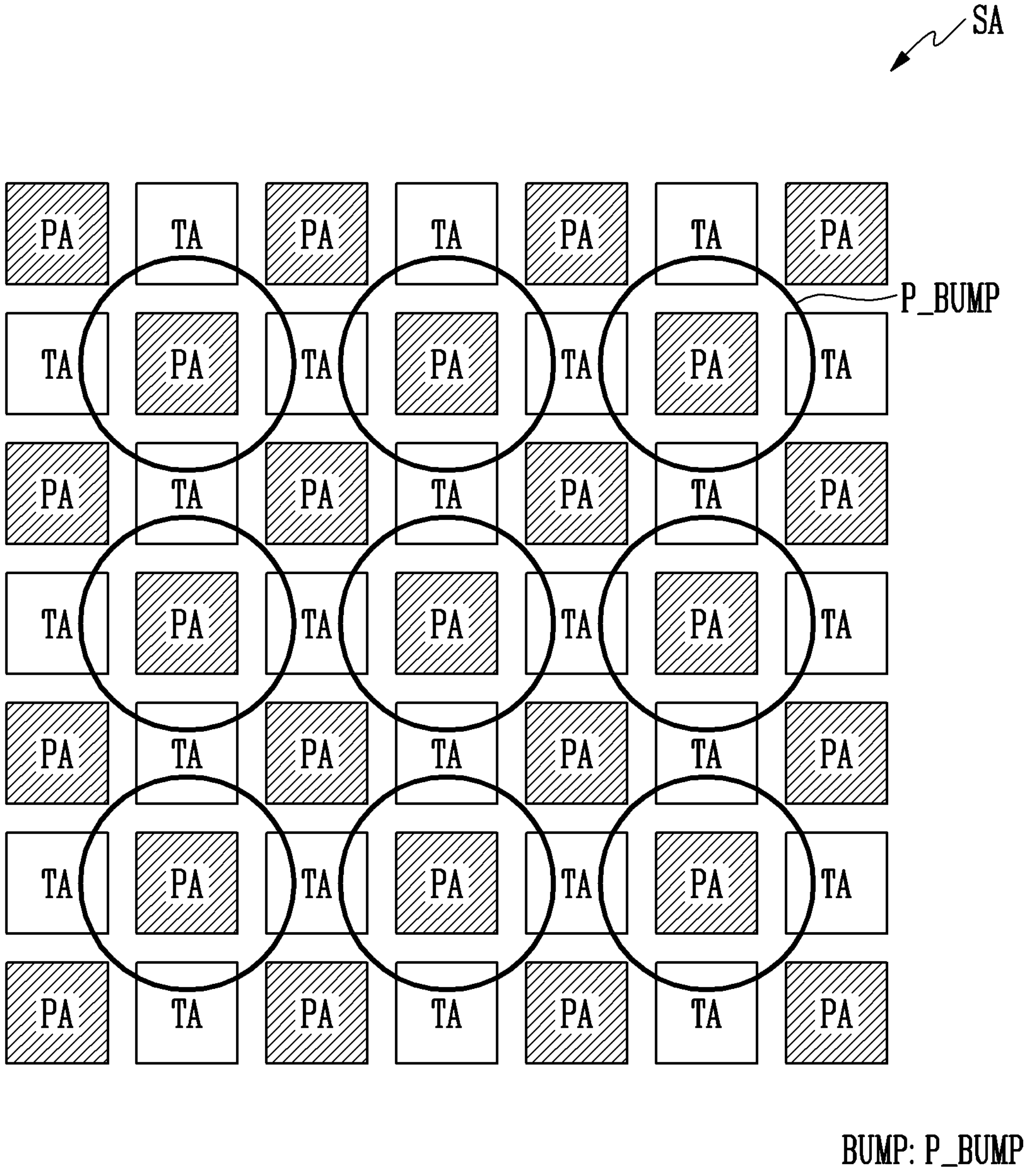
FIG. 15A to FIG. 15D are plan views of embodiments of the bump of FIG. 14A including bump patterns arranged in association with the display panel of FIG. 14C.

In an embodiment, as shown in FIG. 15A, each of the bump patterns P_BUMP may overlap one pixel area PA in a plan view. In other words, each of the bump patterns P_BUMP may be disposed between the transmissive areas TA adjacent to each other among the transmissive areas TA in a plan view. In this case, the bump patterns P_BUMP hardly overlap the transmissive areas TA, and transmittance of light through the transmissive areas TA may be improved.

Figure 15B:
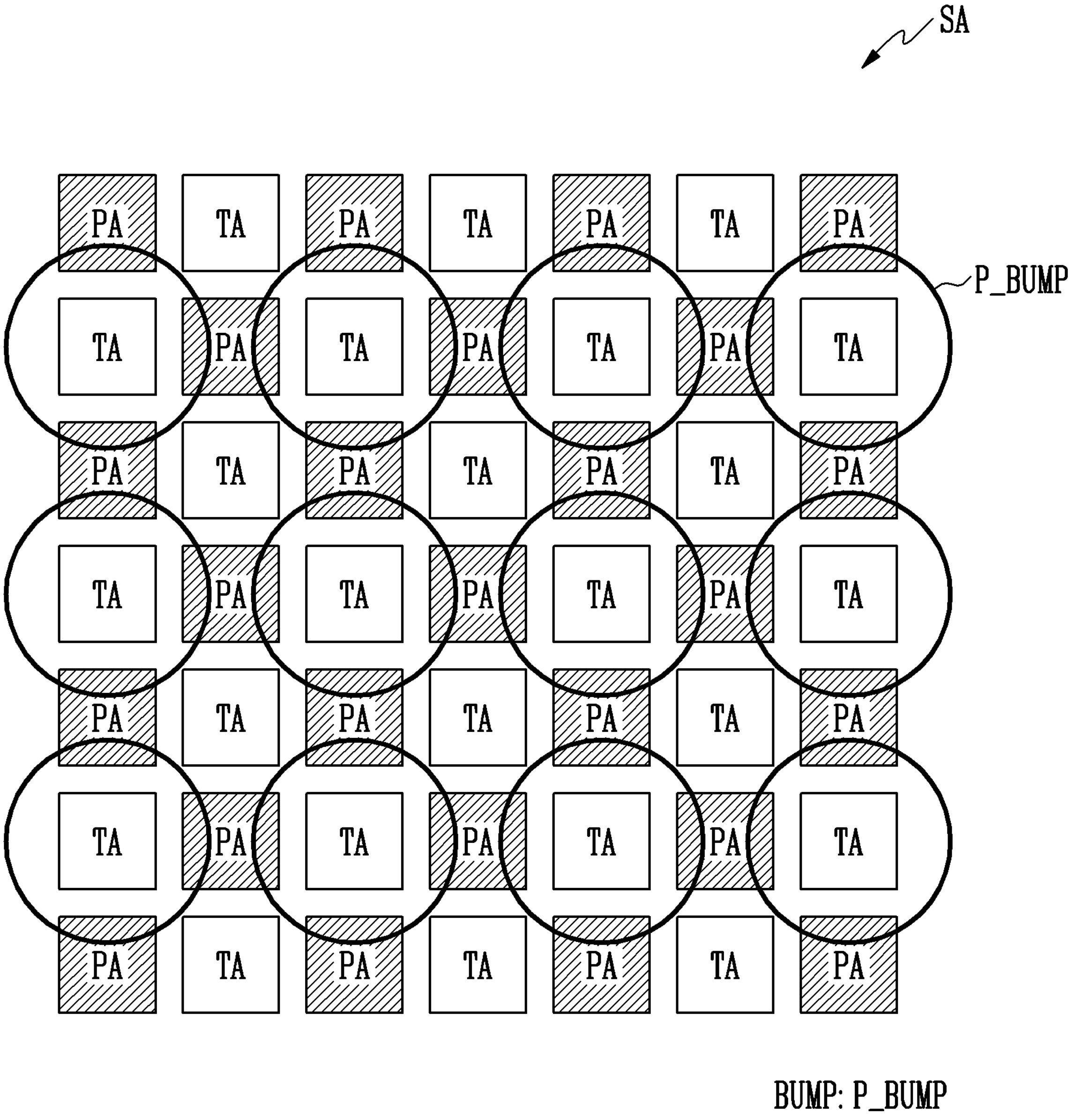

In another embodiment, each of the bump patterns P_BUMP may overlap some of the transmissive areas TA in a plan view. As shown in FIG. 15B, each of the bump patterns P_BUMP may overlap one transmissive area TA in a plan view. In this case, the transmissive area TA may be disposed between the bump patterns P_BUMP adjacent in a diagonal direction, or the transmissive area TA may be exposed in an area surrounded by four bump patterns P_BUMP. Particularly, when the bump patterns P_BUMP have a generally circular planar shape, the transmissive area TA may be completely exposed between the four bump patterns P_BUMP. In the case where the resolution of the photo sensor PPG is similar to the resolution (or density) of the bump patterns P_PUMP, even when the bump patterns P_PUMP shown in FIG. 15B are arranged to overlap some of the the transmissive areas TA, the amount of transmittance of light emitted from or incident on the photo sensor PPG (see FIG. 14A) may be maximized or provided as desired.

Figure 15C:
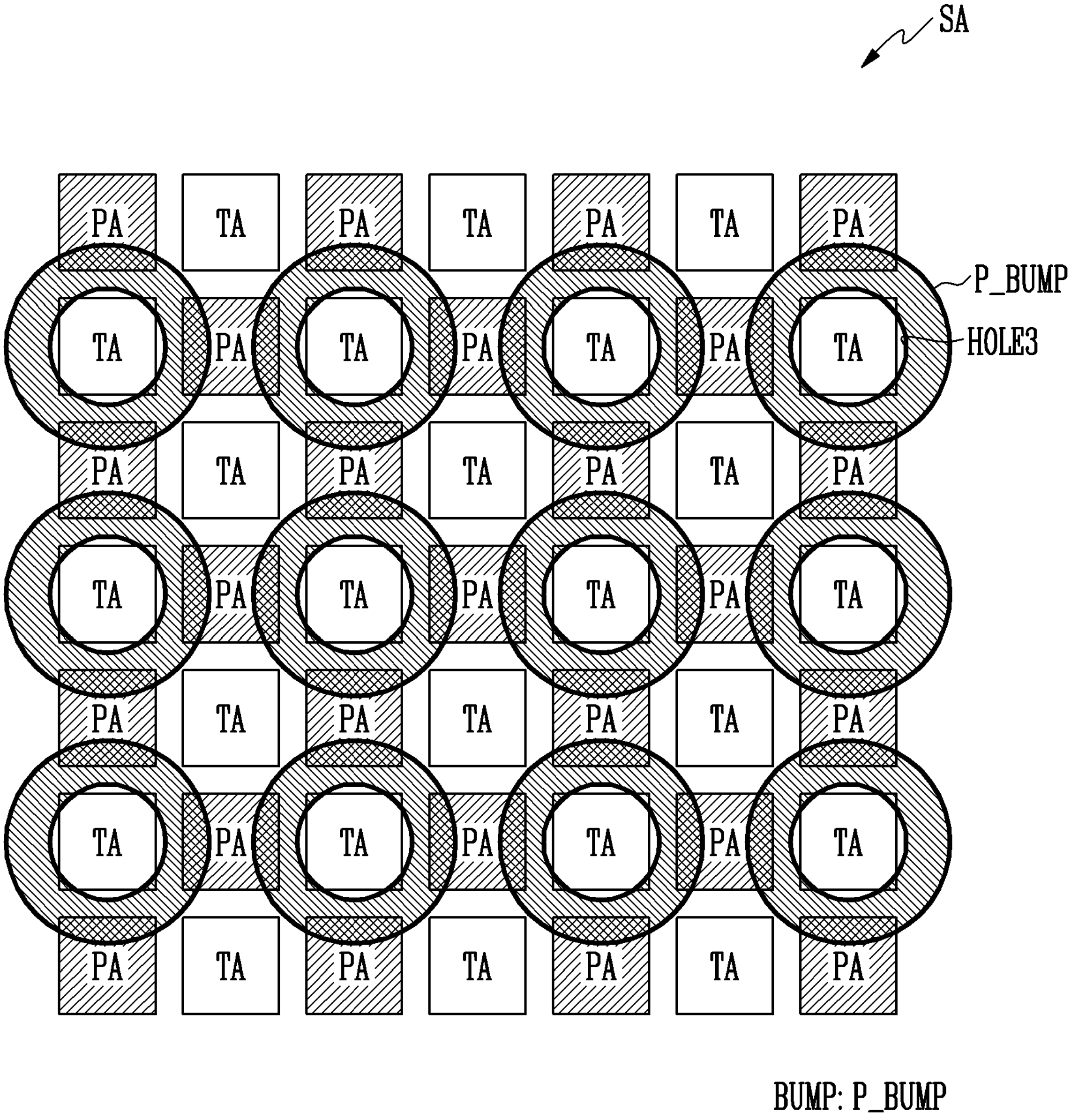

In another embodiment, as shown in FIG. 15C, each of the bump patterns P_BUMP is disposed to overlap some of the transmissive area TA in a plan view, but the third hole HOLE3 may be formed in each of the bump patterns P_BUMP. The third hole HOLE3 may have a size (or area) corresponding to the transmissive area TA, and may overlap the transmissive area TA. In this case, the transmissive area TA may be exposed through the third hole HOLE3. In the case where the resolution of the photo sensor PPG is greater than the resolution (or density) of the bump patterns P_PUMP, or similar to the resolution of the transmissive area TA, the transmittance of light emitted from or incident on the photo sensor PPG (see FIG. 14A) may be maximized, through the arrangement of the bump patterns P_PUMP and the structure of the bump pattern P_BUMP shown in FIG. 15C.

Figure 15D:
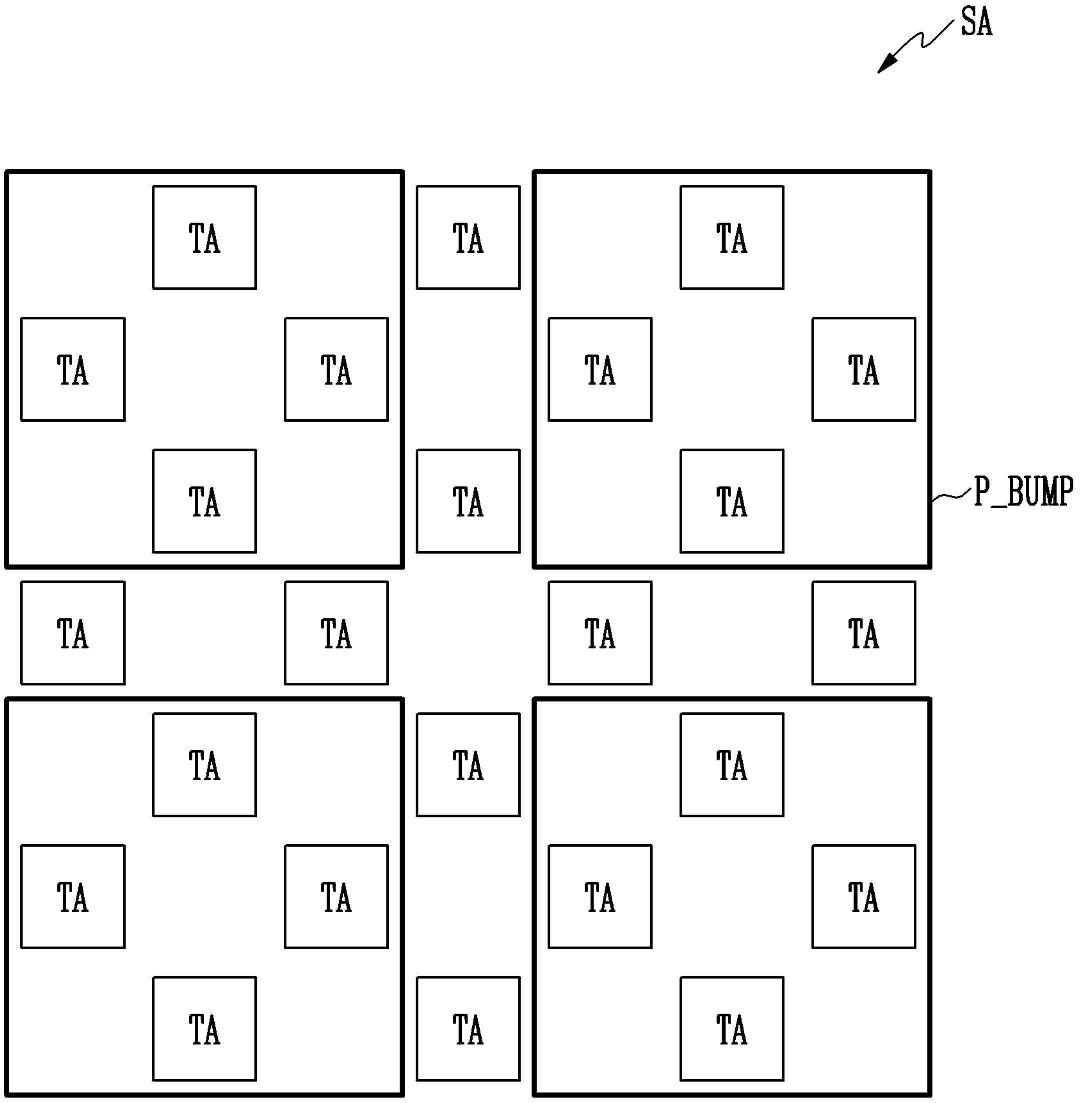

While FIG. 15A to FIG. 15C illustrate that each of the bump patterns P_BUMP has a size (or area) similar to the transmissive area TA or pixel area PA, embodiments are not limited thereto. For example, as shown in FIG. 15D, the bump patterns P_BUMP may have a size (or area) corresponding to a plurality of transmissive areas TA and/or a plurality of pixel areas PA. In this case, the bump patterns P_BUMP may be arranged so that at least some of the transmissive areas TA are exposed between adjacent bump patterns P_BUMP. FIG. 15D illustrates that each of the bump patterns P_BUMP has a generally quadrangular planar shape, but this is an example, and for example, as shown in FIG. 15B, each of the bump patterns P_BUMP may have a generally circular planar shape.

As described with reference to FIG. 15A to FIG. 15D, the bump pattern P_BUMP may overlap at least one transmissive area TA (or, first opening OP1 (see FIG. 14A) or at least one pixel area PA. In addition, when the bump pattern P_BUMP overlaps the transmissive area TA, the third hole HOLE3 exposing the transmissive area TA may be formed in the bump pattern P_BUMP. Accordingly, the amount of light emitted from the photo sensor PPG or received by the photo sensor PPG may increase, sensitivity of the photo sensor PPG may be improved, and accuracy of the blood pressure measurement may be improved.

Figure 16:
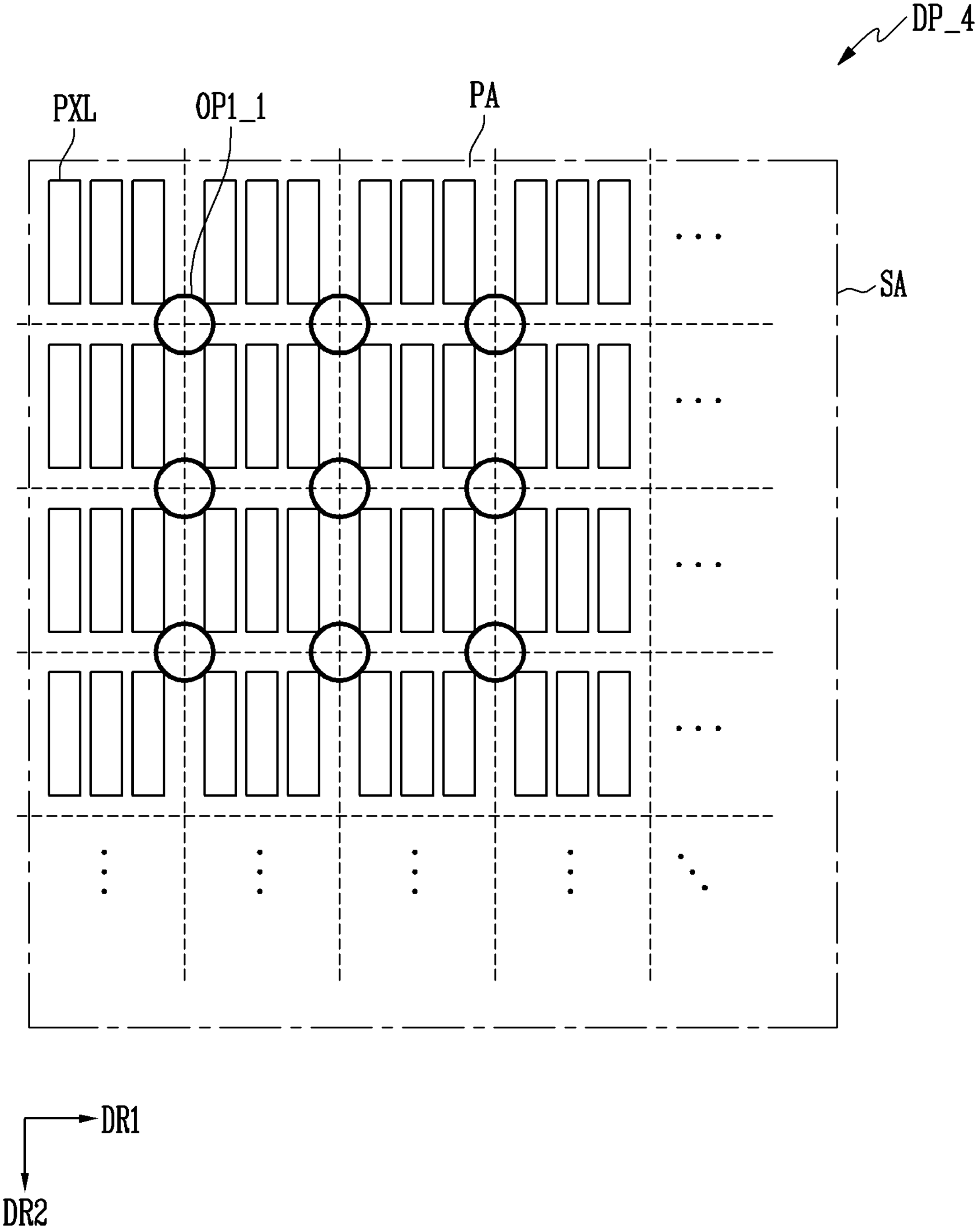
FIG. 16 is a plan view of another embodiment of the display panel of FIG. 14A.

FIG. 16 is a plan view of another embodiment of the display panel of FIG. 14A.

Referring to FIG. 14A, FIG. 14C, and FIG. 16, while the display panel DP_3 of FIG. 14C includes a separate transmissive area TA (or first opening OP1) from which the pixels PXL are removed, the display panel DP_4 of FIG. 16 includes a first opening OP1_1 disposed between the pixels PXL without changing the pixels PXL.

Except for the planar size and position thereof, since the first opening OP1_1 is substantially the same as or similar to the first opening OP1 described with reference to FIG. 14A and FIG. 14B, redundant descriptions will not be repeated to avoid redundancy.

The first opening OP1_1 (or fine hole) may be disposed in an area that does not overlap the pixels PXL in a plan view. That is, the first opening OP1_1 may be formed in an area in which the pixels PXL and the conductive patterns (or wires) connected to the pixels PXL are not disposed. Accordingly, the diameter of the first opening OP1_1 (or a planar size) may be smaller than or substantially equal to a separation distance between the pixels PXL.

As shown in FIG. 16, the first opening OP1_1 may be disposed between four pixels PXL adjacent to each other in the first direction DR1 and the second direction DR2. In addition, the first openings OP1_1 may be spaced apart from each other by a first interval corresponding to widths of a plurality of pixels PXL (for example, three pixels PXL) in the first direction DR1. In addition, the first openings OP1_1 may be spaced apart from each other by a second interval corresponding to a length of one pixel PXL in the second direction DR2. However, this is illustrative, and the first interval in the first direction DR1 and the second interval in the second direction DR2 between the first openings OP1_1 are not limited thereto. In consideration of the resolution of the photo sensor PPG (see FIG. 14A), the first interval and the second interval may be variously set.

As described with reference to FIG. 15D, the bump patterns may be arranged to expose at least some of the first openings OP_1 between adjacent bump patterns. In some embodiments, as described with reference to FIG. 15C, the third hole HOLE3 overlapping first openings OP1_1 may be formed in the bump patterns.

As described with reference to FIG. 16, the display panel DP_4 may include the first openings OP1_1 (or fine holes) formed in an area in which the pixels PXL and the conductive patterns (or wires) connected to the pixels are not disposed. Accordingly, the amount of light emitted from the photo sensor PPG or received by the photo sensor PPG may increase, sensitivity of the photo sensor PPG may be improved, and accuracy of the blood pressure measurement may be improved.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A display device comprising:

a display panel having a plurality of light emitting elements to display an image, the display panel including a first area, the first area including at least some of the plurality of light emitting elements and having a first hole;

a blood pressure sensor disposed adjacent to the display panel to sense pressure applied to at least a portion of the first area and to sense light incident thereon; and a pressure transmission member overlapping the first area of the display panel and the blood pressure sensor, the pressure transmission member comprises a second hole overlapping the first hole, the second hole having the same size as the first hole and being aligned with the first hole along a first direction and a second direction intersecting the first direction, wherein the blood pressure sensor comprises:

a first sensor under the pressure transmission member to sense pressure; and a second sensor overlapping the first sensor in a plan view to sense light transmitted through the display panel, and wherein the first and second sensor are at a same side of the pressure transmission member, wherein the pressure transmission member comprises patterns that are spaced apart from each other in a plan view, and wherein the second hole is surrounded by the patterns.

2. The display device of claim 1, wherein the pressure transmission member comprises a metallic material.

3. The display device of claim 1, wherein the pressure transmission member is disposed between the display panel and the blood pressure sensor.

4. The display device of claim 3, wherein the pressure transmission member comprises a bump having a planar size smaller than or equal to that of the blood pressure sensor.

5. The display device of claim 3, wherein the blood pressure sensor is disposed under the display panel.

6. The display device of claim 5, wherein the second sensor comprises a photo sensor including a light source to emit infrared light or green light.

7. The display device of claim 5, wherein the second sensor comprises a photo sensor to sense light emitted from the display panel and then reflected from a target object.

8. The display device of claim 5, further comprising: a driver to calculate blood pressure based on a pressure sensing signal provided from the first sensor and a light sensing signal provided from the second sensor.

9. The display device of claim 5, wherein the first sensor comprises a pressure sensor including first electrodes extending in a first direction and second electrodes extending in a second direction intersecting the first direction and partially overlapping the first electrodes, and wherein the patterns are respectively disposed in second areas in which the first and second electrodes overlap each other in a plan view.

10. The display device of claim 9, wherein each of the patterns comprises a bump pattern having a planar size smaller than or equal to that of each of the second areas.

11. The display device of claim 1, wherein the pressure transmission member includes patterns that are spaced apart from each other in a plan view, and wherein the patterns are arranged along an edge of the second hole.

12. The display device of claim 11, wherein the first sensor comprises a pressure sensor including first electrodes extending in a first direction in a plan view and second electrodes extending in a second direction intersecting the first direction and partially overlapping the first electrodes, and wherein the patterns are respectively disposed in second areas in which the first and second electrodes overlap in a plan view.

13. The display device of claim 12, wherein the patterns include third holes.

14. The display device of claim 1, wherein the pressure transmission member comprises patterns that are spaced apart from each other in a plan view, and wherein the patterns are disposed over the first area excluding the second hole.

15. The display device of claim 1, further comprising:

a bracket disposed under the blood pressure sensor, wherein the pressure transmission member is disposed between the blood pressure sensor and the bracket.

16. The display device of claim 1, wherein the pressure transmission member is disposed between the first sensor and the second sensor.

17. The display device of claim 1, further comprising:

a window disposed on the display panel, wherein the pressure transmission member is disposed between the display panel and the window.

18. The display device of claim 1, wherein the display panel comprises:

a first substrate;

a light emitting element layer disposed on the first substrate and including the light emitting elements;

a first passivation layer disposed on the light emitting element layer; and a second passivation layer disposed under the first substrate, and wherein the pressure transmission member is disposed between the first substrate and the second passivation layer.

19. A display device comprising:

a display panel having a plurality of light emitting elements to display an image, the display panel including a first area, the first area having a first hole;

a blood pressure sensor disposed adjacent to the display panel to sense pressure applied to at least a portion of the first area and to sense light incident thereon; and a pressure transmission member overlapping the first area of the display panel and the blood pressure sensor, the pressure transmission member comprises a second hole overlapping the first hole, the second hole having the same size as the first hole and being aligned with the first hole along a first direction and a second direction intersecting the first direction, wherein the blood pressure sensor comprises:

a first sensor under the pressure transmission member to sense pressure; and a second sensor overlapping the first sensor in a plan view to sense light transmitted through the display panel, wherein the first and second sensor are at a same side of the pressure transmission member, wherein the pressure transmission member comprises patterns that are spaced apart from each other in a plan view, wherein the second hole is surrounded by the patterns, and wherein the display panel includes openings disposed in the first area of the display panel without overlapping the light emitting elements and conductive patterns connected to the light emitting elements.

20. The display device of claim 19, wherein the display panel includes a light-transmissive material inside each of the openings, and wherein the light-transmissive material includes at least one of germanium, silicon, zinc selenide (ZnSe), silicon dioxide ($SiO_2$), polyethylene, and polystyrene.

21. The display device of claim 19, wherein each of the patterns is disposed between adjacent ones of the openings in a plan view.

22. The display device of claim 19, wherein the pressure transmission member comprises patterns that are spaced apart from each other in a plan view, and wherein each of the patterns is disposed to overlap some of the openings in a plan view.

23. The display device of claim 22, wherein the patterns comprise third holes overlapping the some of the openings.

24. A display device comprising:

a display panel having a plurality of light emitting elements to display an image, the display panel including a first area, the first area including at least some of the plurality of light emitting elements and having a first hole;

a pressure sensor disposed on the display panel to sense a pressure applied to at least a portion of the first area;

a photo sensor disposed under the display panel to sense light incident thereon;

a pressure transmission member disposed on the display panel and overlapping the pressure sensor, the pressure transmission member comprises a second hole overlapping the first hole, the second hole having the same size as the first hole and being aligned with the first hole along a first direction and a second direction intersecting the first direction; and a driver to generate a blood pressure signal based on a pressure sensing signal provided from the pressure sensor and a light sensing signal provided from the photo sensor, wherein the pressure sensor comprises:

a first sensor under the pressure transmission member to sense pressure; and a second sensor overlapping the first sensor in a plan view to sense light transmitted through the display panel, wherein the first and second sensor are at a same side of the pressure transmission member, wherein the pressure transmission member comprises patterns that are spaced apart from each other in a plan view, and wherein the second hole is surrounded by the patterns.

25. The display device of claim 24, further comprising:

a window disposed on the pressure sensor, wherein the pressure transmission member is disposed between the window and the pressure sensor.

26. The display device of claim 24, wherein the pressure transmission member is disposed between the pressure sensor and the display panel.

27. The display device of claim 24, wherein the patterns are arranged along an edge of the second hole.

28. The display device of claim 27, wherein the pressure sensor comprises first electrodes extending in a first direction in a plan view and second electrodes extending in a second direction intersecting the first direction and partially overlapping the first electrodes, and wherein the patterns are respectively disposed in second areas in which the first and second electrodes overlap each other in a plan view.

29. The display device of claim 28, wherein the patterns comprise third holes.

* * * * *